United States Patent
Leff et al.

(10) Patent No.: US 11,589,902 B2
(45) Date of Patent: Feb. 28, 2023

(54) POLY AXIAL SCREW AND LOCKING CAP

(71) Applicant: GLOBUS MEDICAL, INC., Audubon, PA (US)

(72) Inventors: David Leff, Philadelphia, PA (US); David Peretz, Wynnewood, PA (US); Matthew Bechtel, Philadelphia, PA (US); Patrick Murray, Collegeville, PA (US); Noah Hansell, King of Prussia, PA (US)

(73) Assignee: Globus Medical Inc., Audubon, PA (US)

( * ) Notice: Subject to any disclaimer, the term of this patent is extended or adjusted under 35 U.S.C. 154(b) by 32 days.

(21) Appl. No.: 16/707,329

(22) Filed: Dec. 9, 2019

(65) Prior Publication Data
US 2021/0169535 A1    Jun. 10, 2021

(51) Int. Cl.
*A61B 17/70* (2006.01)

(52) U.S. Cl.
CPC ...... *A61B 17/7037* (2013.01); *A61B 17/7002* (2013.01); *A61B 17/7032* (2013.01); *A61B 17/7035* (2013.01); *A61B 17/7082* (2013.01); *A61B 17/7091* (2013.01); *A61B 2560/0431* (2013.01)

(58) Field of Classification Search
CPC ......... A61B 17/7032–17/7037; A61B 17/7091
See application file for complete search history.

(56) References Cited

U.S. PATENT DOCUMENTS

| | | | | |
|---|---|---|---|---|
| 8,574,274 B2 * | 11/2013 | Courtney | ........... | A61B 17/7034 606/305 |
| 8,747,445 B2 * | 6/2014 | Hawkins | ............ | A61B 17/7032 606/305 |
| 2003/0100904 A1 * | 5/2003 | Biedermann | ...... | A61B 17/7032 606/272 |
| 2004/0049196 A1 * | 3/2004 | Jackson | ................ | F16B 35/047 606/916 |
| 2004/0138660 A1 * | 7/2004 | Serhan | ............... | A61B 17/7032 606/272 |
| 2006/0293666 A1 * | 12/2006 | Matthis | .............. | A61B 17/7032 606/86 A |
| 2012/0123431 A1 * | 5/2012 | Robinson | ............. | A61B 17/808 606/104 |
| 2013/0131730 A1 * | 5/2013 | Jackson | ............. | A61B 17/7032 606/278 |
| 2013/0345761 A1 * | 12/2013 | Biedermann | ...... | A61B 17/7037 606/306 |

* cited by examiner

*Primary Examiner* — Julianna N Harvey

(57) ABSTRACT

Systems, methods, and devices for securing a spinal rod are provided. A clamp assembly comprises a tulip comprising an opening comprising an inner surface, wherein the inner surface is threaded; and a threaded locking cap disposed in the opening, wherein threads of the locking cap and the inner surface include various geometries.

12 Claims, 25 Drawing Sheets

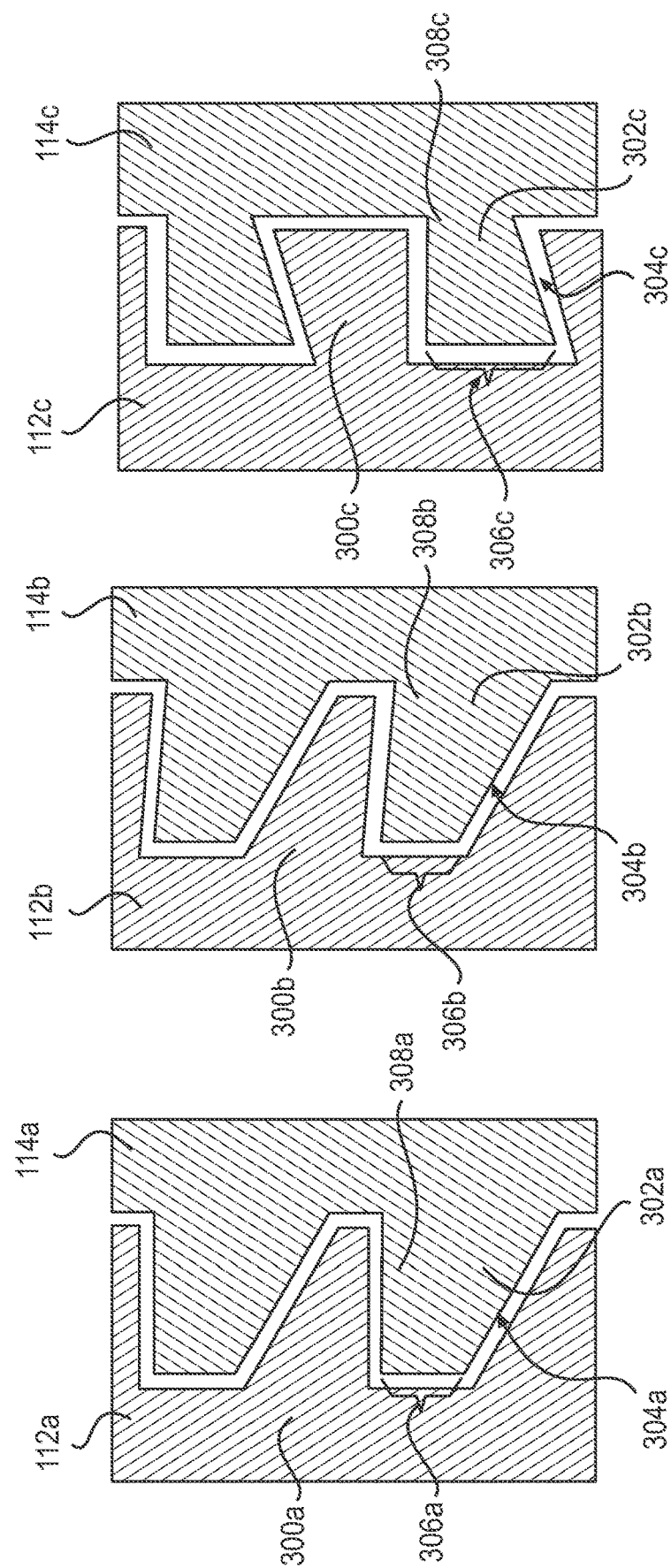

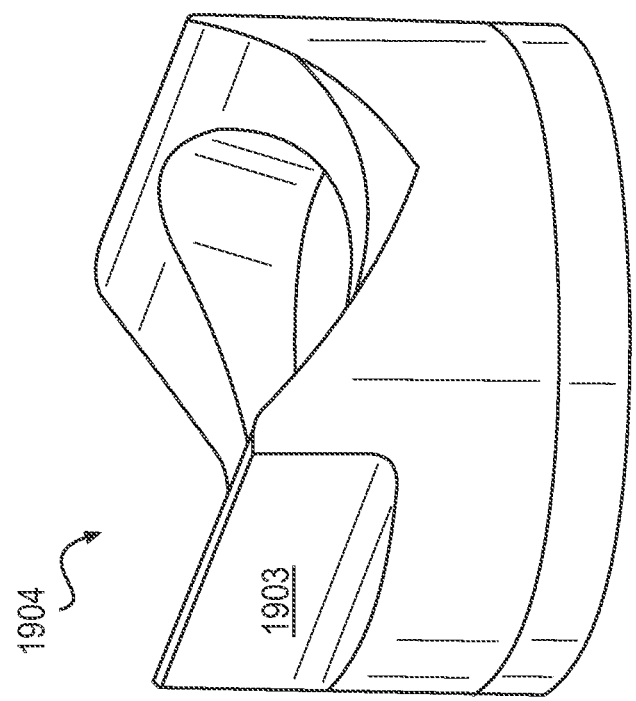
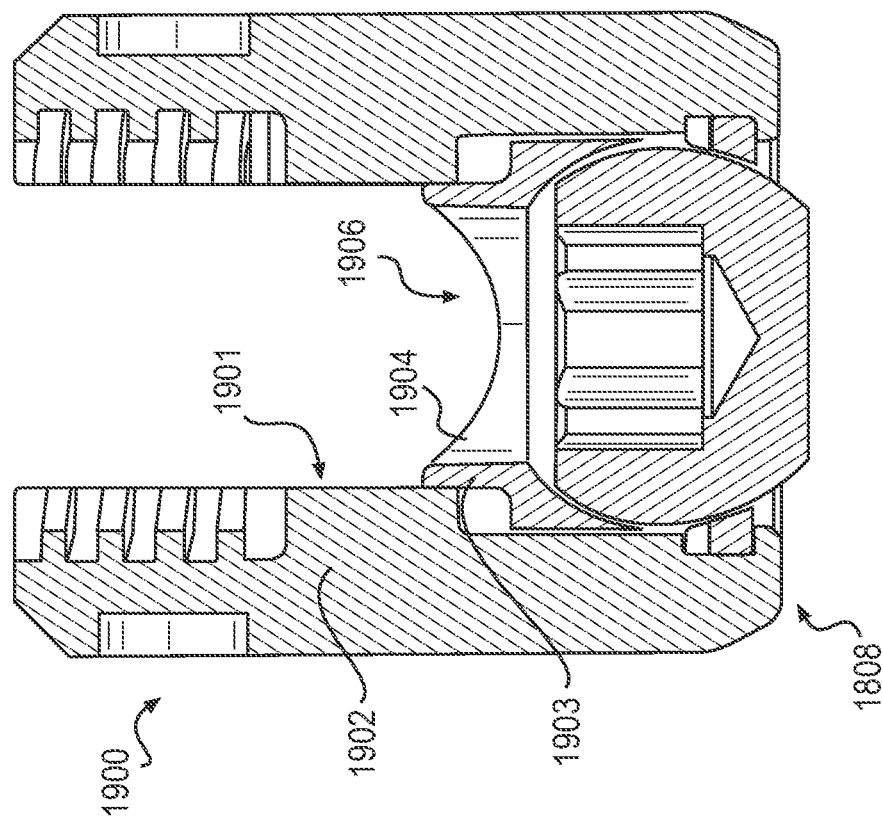
FIG. 19B
FIG. 19A

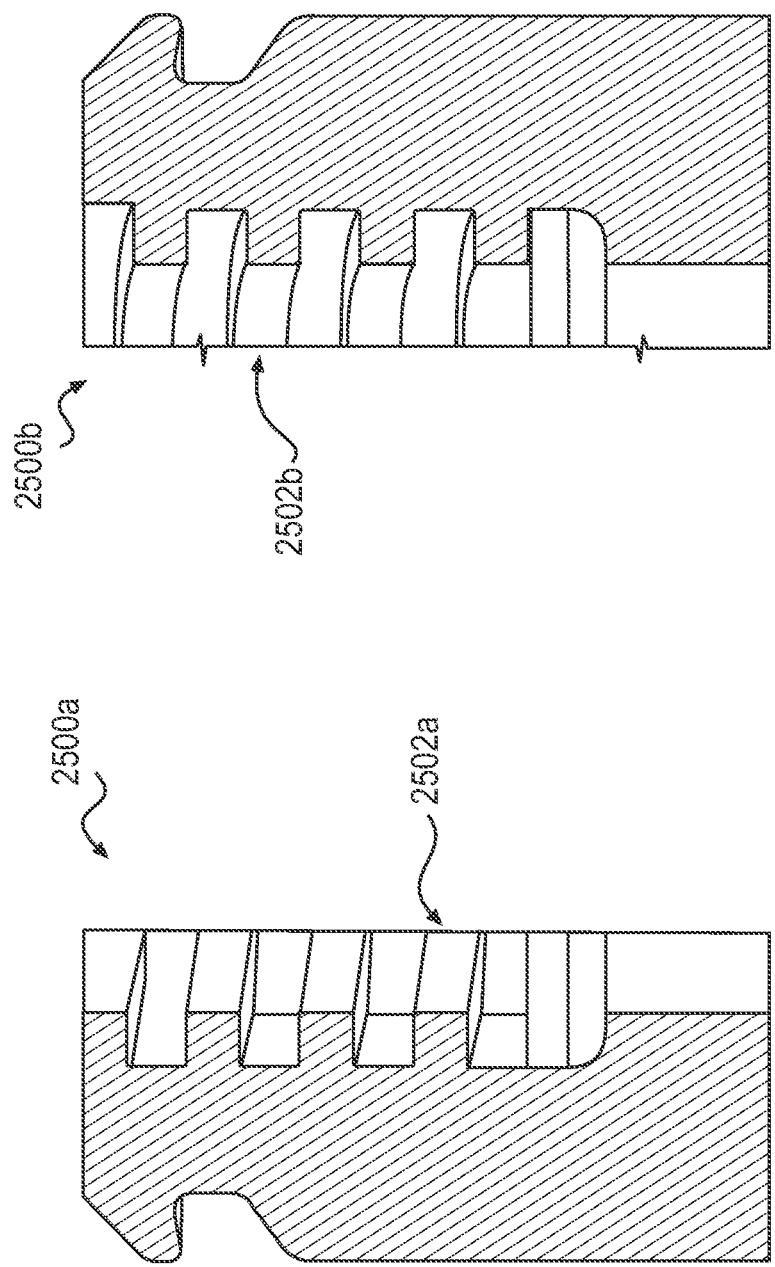

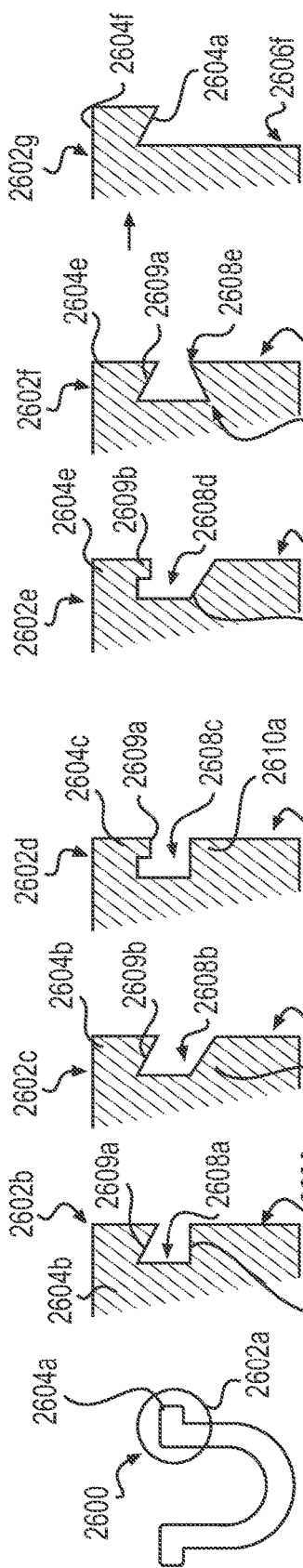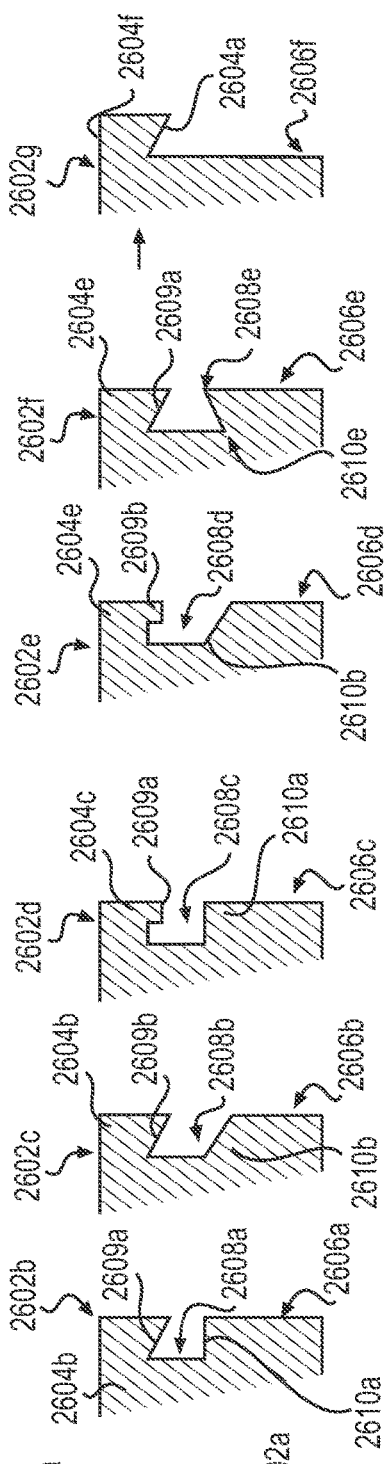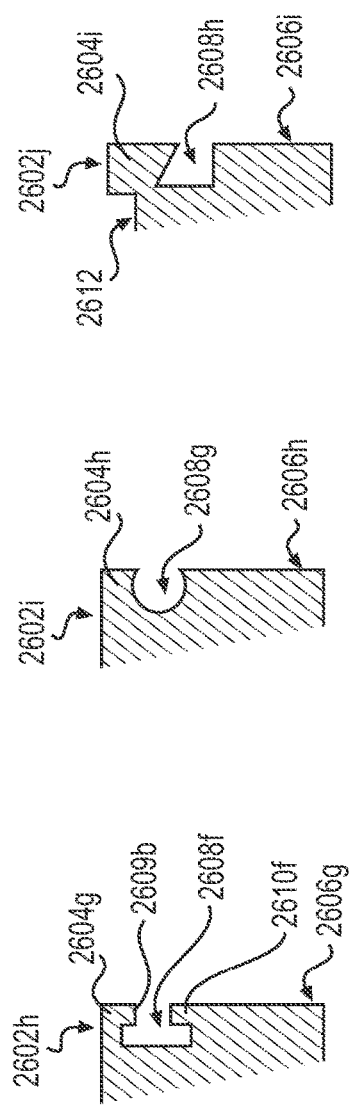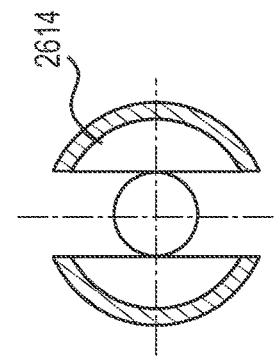

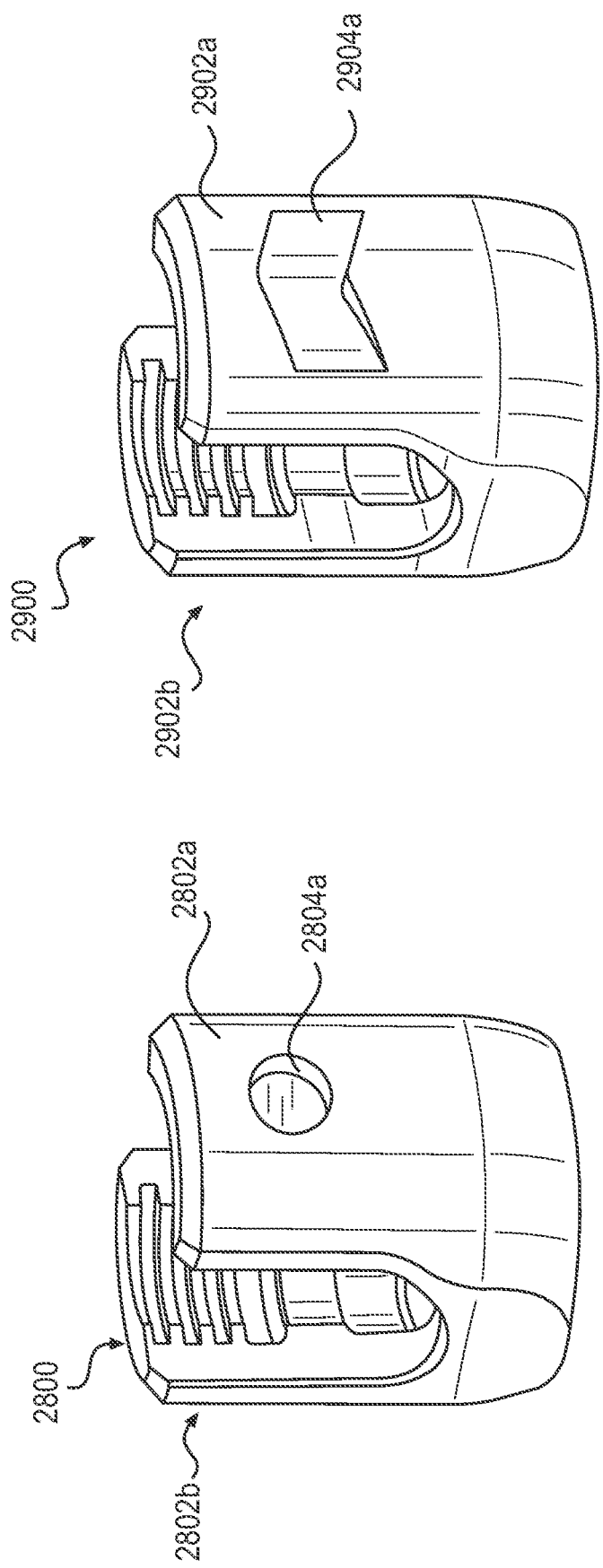

POLYAXIAL SCREW AND LOCKING CAP

BACKGROUND

Many types of spinal irregularities cause pain, limit range of motion, or injure the nervous system within the spinal column. These irregularities can result from trauma, tumor, disc degeneration, or disease. Typically, these irregularities are treated by immobilizing a portion of the spine. This treatment typically involves affixing a plurality of components, such as, for example, screws, hooks, and/or clamps, to one or more vertebrae, and attaching the components to an elongated rod that stabilizes the vertebrae.

SUMMARY

In an exemplary embodiment, the present disclosure provides a clamp assembly comprising a tulip comprising an opening comprising an inner surface, wherein the inner surface is threaded; and a threaded locking cap disposed in the opening, wherein threads of the locking cap and the inner surface include various geometries.

In another exemplary embodiment, the present disclosure provides a clamp assembly comprising a tulip comprising an opening comprising an inner surface, wherein the inner surface is threaded; and a threaded locking cap disposed in the opening, wherein the threaded locking cap includes a drive feature, wherein the drive feature includes various geometries.

In another exemplary embodiment, the present disclosure provides a clamp assembly comprising a tulip, wherein an inner surface of the tulip comprises threads; and a drive feature positioned in an outer portion of the tulip, the drive feature configured to receive a driving instrument, wherein the drive feature includes various geometries.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

FIG. 3A illustrates a first type of buttress threads of a clamp assembly in accordance with particular embodiments of the present disclosure;

FIG. 3B illustrates a second type of buttress threads of a clamp assembly in accordance with particular embodiments of the present disclosure;

FIG. 3C illustrates a bottom positive angle thread of a clamp assembly in accordance with particular embodiments of the present disclosure;

FIG. 19A illustrates a side cross-sectional view of another clamp assembly in accordance with particular embodiments of the present disclosure;

FIG. 19B illustrates a perspective view of a saddle in accordance with particular embodiments of the present disclosure;

FIG. 25A illustrates a portion of an inner surface of a tulip in accordance with particular embodiments of the present disclosure;

FIG. 25B illustrates a portion of an inner surface of another tulip in accordance with particular embodiments of the present disclosure;

FIGS. 26A-26K illustrate various geometries of an upper portion of a tulip in accordance with particular embodiments of the present disclosure;

FIGS. 27-29 illustrate various features positioned on an outer surface of a tulip in accordance with particular embodiments of the present disclosure;

DETAILED DESCRIPTION

Figure 2:
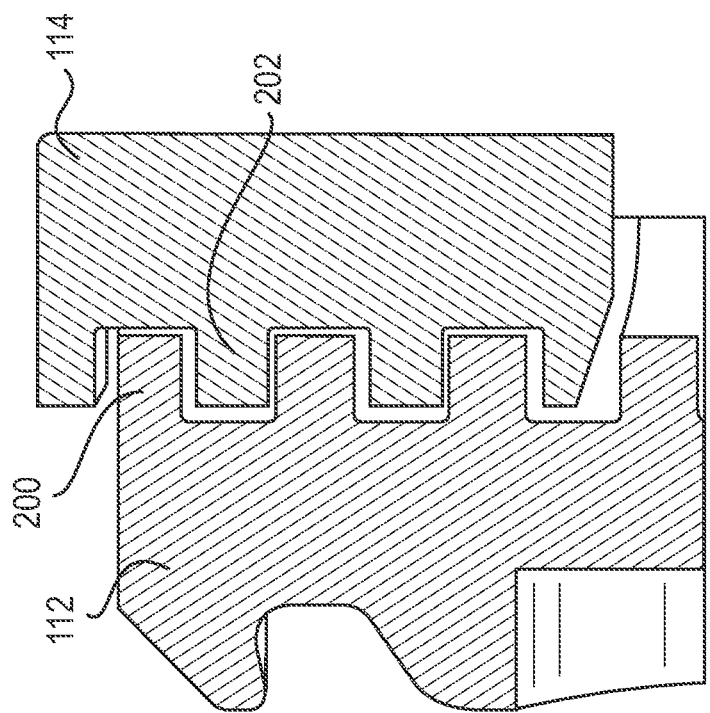
FIG. 2 illustrates square threads of a clamp assembly in accordance with particular embodiments of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments generally relate to spinal surgery. More particularly, embodiments relate to systems, methods, and devices for securing a spinal rod and a pedicle screw with a clamp assembly.

The clamp assembly can be utilized for open and percutaneous approaches to the posterior spine. The clamp assembly can be used on multiple types of pedicle screws such as polyaxial, uniplanar, monoaxial, reduction, and modular pedicle screws. The clamp assembly locks or restricts motion of the pedicle screw and the spinal rod. This allows corrective forces to transfer to vertebra for axial derotation, parallel compression, parallel distraction, and/or reduction.

Figure 1:
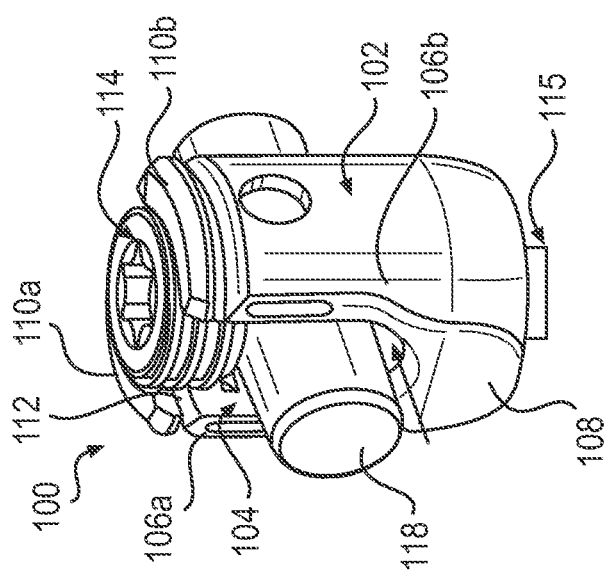
FIG. 1 illustrates a clamp assembly in accordance with particular embodiments of the present disclosure.

FIG. 1 illustrates a clamp assembly ("clamp assembly") 100 in accordance with particular embodiments of the present disclosure. In the illustrated embodiment, the clamp assembly 100 may include a tulip 102 and a threaded locking cap 114 disposable in the tulip 102. A pedicle screw 115 may extend from a bottom portion of the tulip 102. As illustrated, a spinal rod 118 may be held by the tulip 102. By tightening the threaded locking cap 114 into the tulip 102, a spinal rod 118 and pedicle screw 115 may be secured in the tulip 102.

The tulip 102 may be a rigid member that resembles a bullet with a hollow interior. The tulip 102 may include an opening 104 situated between portions 106a and 106b. A curved portion 108 may be disposed between the portions 106a and 106b, as shown. The curved portion 108 may be curved to correspond with a shape of a spinal rod 118. As illustrated, the portions 106a and 106b may be in the form of tabs that extend generally parallel away from the curved portion 108 to distal ends 110a and 110b. In certain embodiments, the opening 104 may be defined between the portions 106a and 106b. In certain embodiments, the opening 104 may extend from the curved portion 108 to distal ends 110a and 110b of the portions 106a and 106b, as shown. Inner surface 112 of the portions 106a and 106b may be threaded.

The threaded locking cap 114 may be disposed within the opening 104, as shown. The spinal rod 118 may extend through the opening 104, and a screw such as the pedicle screw 115 may extend through the curved portion 108. As illustrated, the pedicle screw 115 (or a portion thereof, such as the screw head) may extend into the curved portion 108 of the tulip 102. In accordance with particular embodiments, tightening the threaded locking cap 114 should a saddle component when then compresses against the pedicle screw 115 to restrict motion of the spinal rod 118 and the pedicle screw 115 thereby forming a rigid construct.

Various thread geometries can be used for the inner surface 112 of the tulip 102 and the threaded locking cap 114. Suitable thread geometries may include, but are not limited to, rectangular shaped threads and/or angled threads. FIGS. 2, 3A, 3B, and 3C will describe different thread geometries in accordance with particular embodiments.

FIG. 2 illustrates threads 200 of the inner surface 112 and threads 202 of the threaded locking cap 114 in accordance with particular embodiments of the present disclosure. As shown, the threads 200 and 202 are straight or rectangular shaped (e.g., square shaped).

FIG. 3A illustrates threads 300a (e.g., buttress threads) of an inner surface 112a and threads 302a of a threaded locking cap 114a in accordance with particular embodiments of the present disclosure. As shown, a bottom surface 304a of a thread 302a may be angled outward away from a minor diameter 306a. A top surface 308a may be flat or angled inward (e.g., top surface 308b shown on FIG. 3B), towards the minor diameter 306a.

FIG. 3B illustrates threads 300b (e.g., buttress threads) of an inner surface 112b and threads 302b of a threaded locking cap 114b in accordance with particular embodiments of the present disclosure. As shown, a bottom surface 304b of a thread 302b may be angled outward away from a minor diameter 306b. A top surface 308b may be flat or angled inward towards the minor diameter 306b.

FIG. 3C illustrates threads 300c of an inner surface 112c and threads 302c of a threaded locking cap 114c in accordance with particular embodiments of the present disclosure.

As shown, a bottom surface 304c of a thread 302c may be angled inward to a minor diameter 306c. A top surface 308c may angled inward or flat.

Figure 4B:
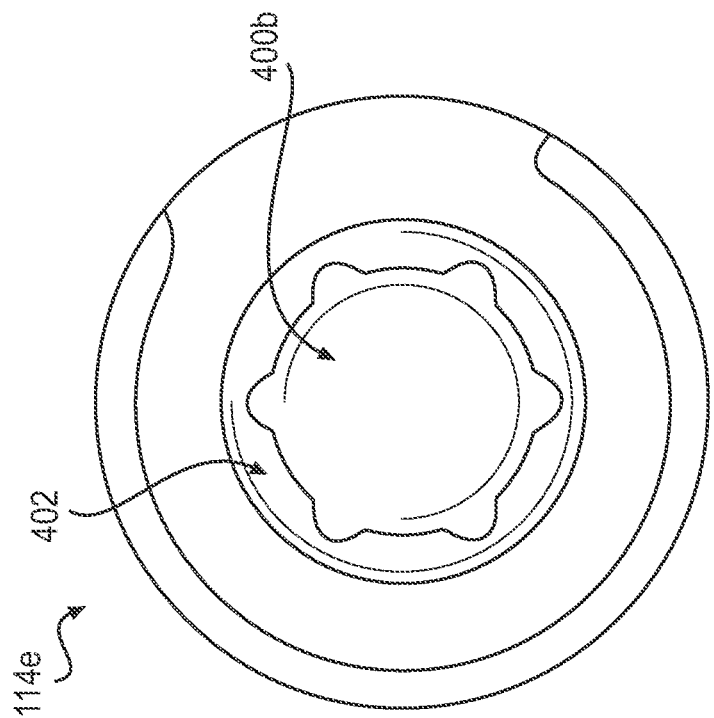
FIG. 4B illustrates a top view of another drive feature of a threaded locking cap in an initial position in accordance with particular embodiments of the present disclosure.
Figure 4A:
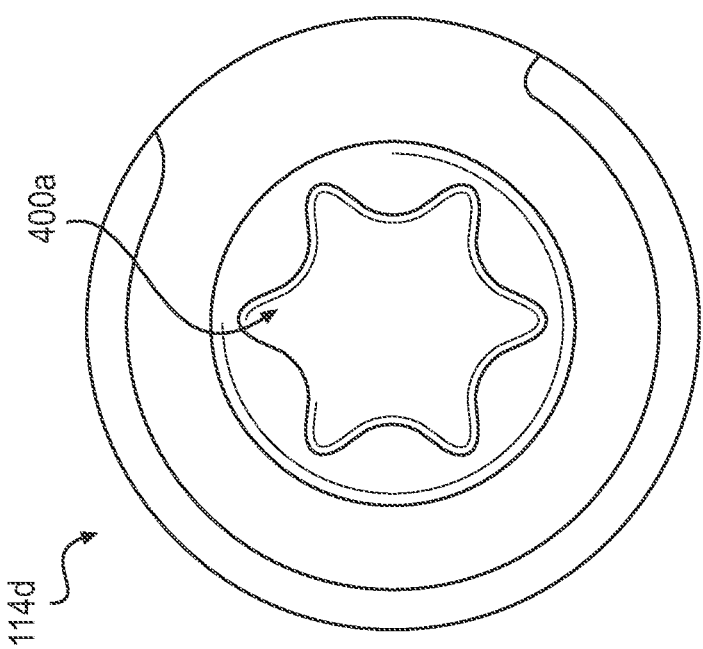
FIG. 4A illustrates a top view of a drive feature of a threaded locking cap in accordance with particular embodiments of the present disclosure.
Figure 5:
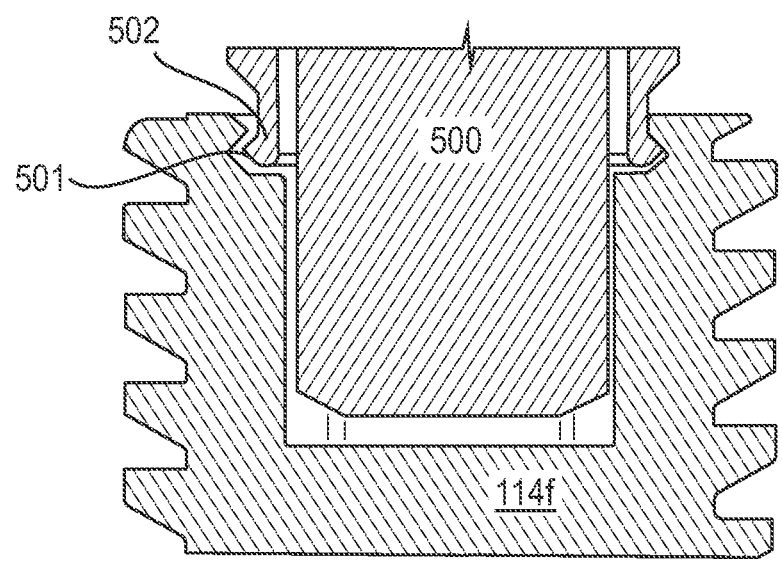
FIG. 5 illustrates a side cross-sectional view of another threaded locking cap and driving instrument in accordance with particular embodiments of the present disclosure.
Figure 6:
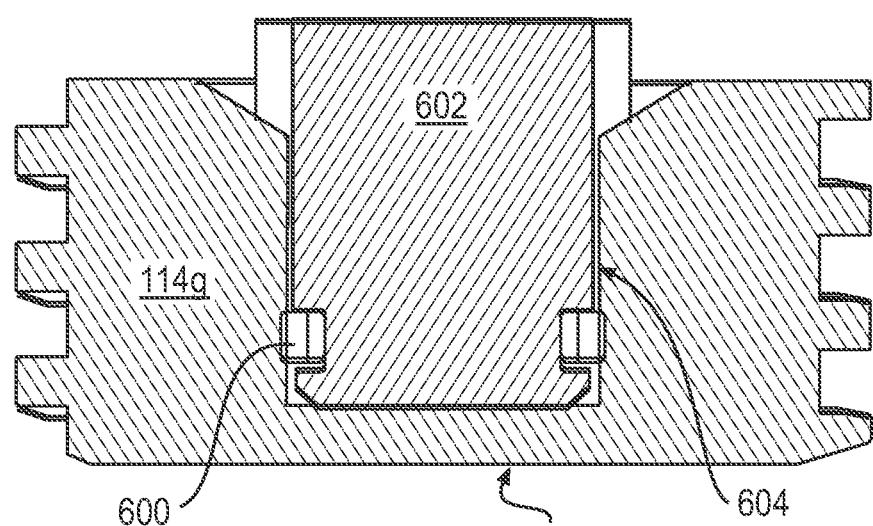
FIG. 6 illustrates a side cross-sectional view of another threaded locking cap and insertion instrument in accordance with particular embodiments of the present disclosure.

In accordance with present embodiments, a driving instrument (e.g., driving instrument 500 on FIG. 5 or driving instrument 602 on FIG. 6) may be used to drive the locking cap 114 into the tulip 104. The locking cap 114 may be include various design features for engagement with the driving instrument. FIGS. 4A and 4B illustrate various drive features on the locking cap 114 into which the driving instrument may be inserted in accordance with particular embodiments. FIGS. 5 and 6 illustrate various features that may be used for retainment of the locking cap 114 by the driving instrument in accordance with particular embodiments. The locking cap 114 may also include various features for contact with the tulip 104. FIGS. 7 to 11 illustrate various features of the locking cap 114 for contact with the tulip 104.

FIG. 4A illustrates a locking cap drive feature ("drive feature") 400a for a locking cap 114d, in accordance with particular embodiments of the present disclosure. The drive feature 400a may be used to insert and tighten the locking cap 114d, and may be a hex, a hexalobe (as shown), or a modified hexalobe (e.g., shown on FIG. 4B). The drive feature 400a may either go partway into or through the locking cap 114d. The drive feature 400a may be formed in a top of the locking cap 114d. In the illustrated embodiment, the drive feature 400a is recessed, but it should be understood the drive feature 400a may also be a protrusion from the locking cap 114d.

FIG. 4B illustrates a locking cap drive feature ("drive feature") 400b for a locking cap 114e, in accordance with particular embodiments of the present disclosure. The drive feature 400b may be used to insert and tighten the locking cap 114e, and may be a hex, a hexalobe, or a modified hexalobe (as shown). The modified hexalobe has inner lobes 402 of a hexalobe truncated by a circle. The drive feature 400b may either go partway into or through the locking cap 114e. The drive feature 400b may be formed in a top of the locking cap 114e. In the illustrated embodiment, the drive feature 400b is recessed, but it should be understood the drive feature 400a may also be a protrusion from the locking cap 114e.

FIG. 5 illustrates a cross-section of a driving instrument 500 positioned within a locking cap 114f in accordance with particular embodiments of the present disclosure. As shown, the locking cap 114f may include grooves 501 to receive spring tabs 502 of a driving instrument 501. The spring tabs 502 may clip into the grooves 500 of the locking cap 114f, for example, to secure the driving instrument 500 to the locking cap 114f. In certain embodiments (not shown), the locking cap 114f can be retained instead by a tapered drive feature on either the locking cap 114f, the driving instrument 501, or both.

FIG. 6 illustrates a cross-section of a split ring 600 housed on a driving instrument 602 in accordance with particular embodiments of the present disclosure. The split ring 600 may be used, for example, to secure the driving instrument 602 to the locking cap 114g. As shown, the split ring 600 may exert radial pressure against a drive feature 604 of a locking cap 114g to retain the locking cap 114g. In certain embodiments, a groove (not shown) may be cut into the drive feature 604 for the split ring 600 to expand into for further retention. The locking cap 114g may include a flat bottom 606, as shown.

Figure 7:
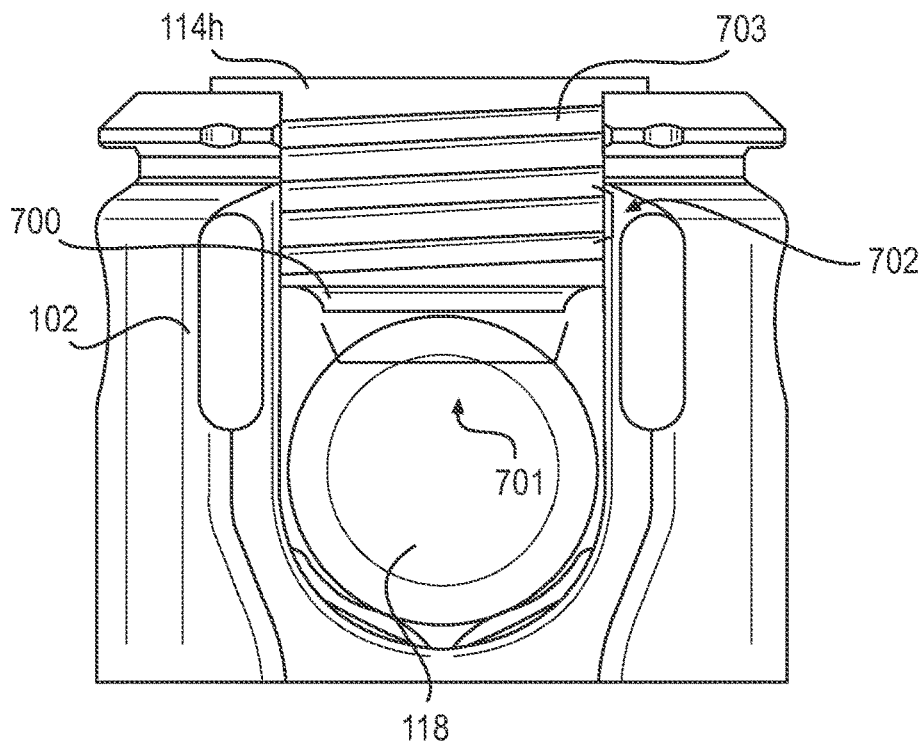
FIG. 7 illustrates a side view of a clamp assembly in accordance with particular embodiments of the present disclosure.

FIG. 7 illustrates a locking cap 114h disposed within the tulip 102, in accordance with particular embodiments of the present disclosure. As shown, a bottom 700 of the locking cap 114h may be flat but have a narrower outer diameter 701 than a minor diameter 702 of threads 703, to provide a more consistent contact with a curvature of the spinal rod 118. However, while FIG. 7 shows the bottom 700 as being flat, it should understood that embodiments of the bottom 700 may be otherwise formed, for example, curved or angled.

Figure 8:
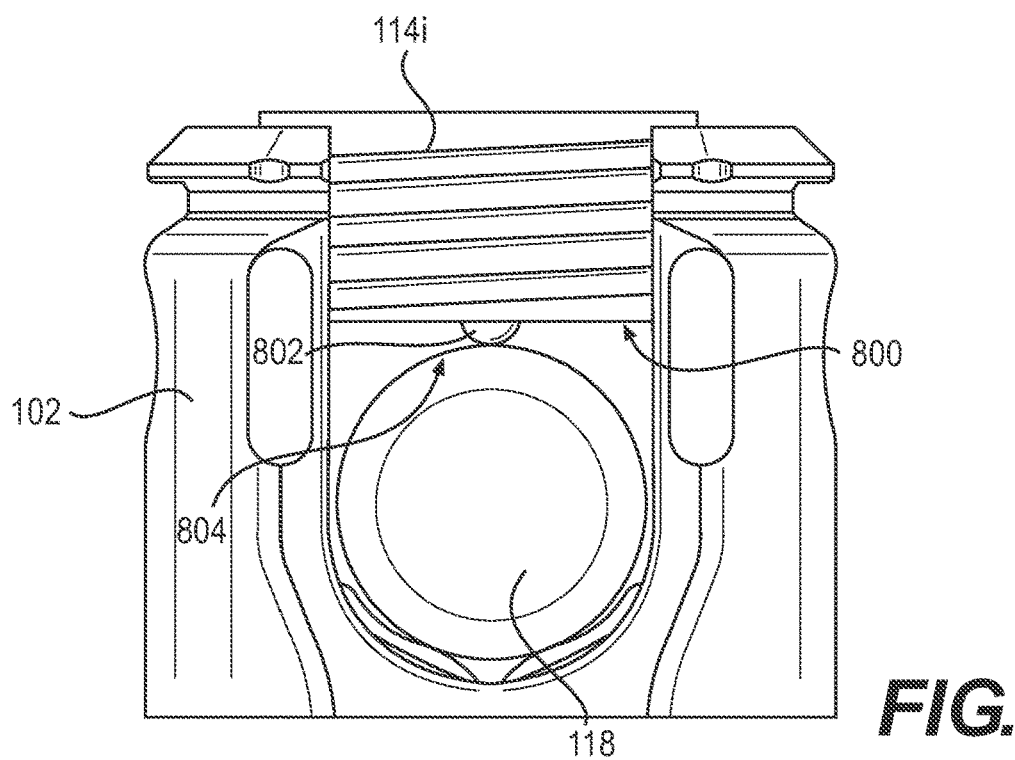
FIG. 8 illustrates a side view of another clamp assembly in accordance with particular embodiments of the present disclosure.

FIG. 8 illustrates a locking cap 114i disposed within the tulip 102, in accordance with particular embodiments of the present disclosure. As shown, a bottom 800 of the locking cap 114i may have a rounded bump 802 to contact the spinal rod 118 at a point 804. The bump 802 may deform or indent the spinal rod 118 or be deformed by the spinal rod 118 to increase grip. The bump 802 may extend from a minor portion of the bottom 800 of the locking cap 114i.

Figure 9:
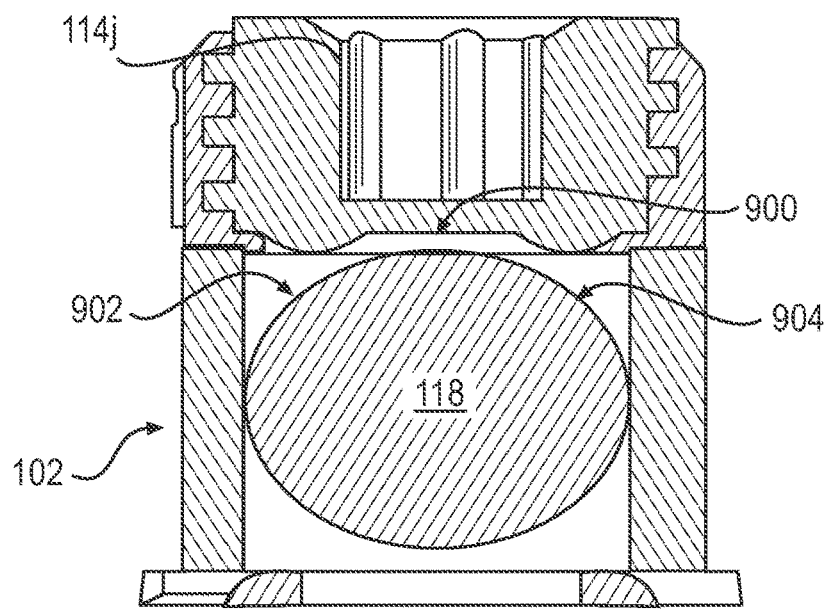
FIG. 9 illustrates a side cross-sectional view of another clamp assembly in accordance with particular embodiments of the present disclosure.

FIG. 9 illustrates a cross-section of a locking cap 114j disposed within a tulip 102, in accordance with particular embodiments of the present disclosure. A bottom 900 of the locking cap 114j may have a rounded ring 900 to contact the spinal rod 118 at two points 902 and 904. The rounded ring 900 may deform or indent to increase grip. In some embodiments, the rounded ring 900 may be raised portion of the bottom 900 of the locking cap 114j.

Figure 10:
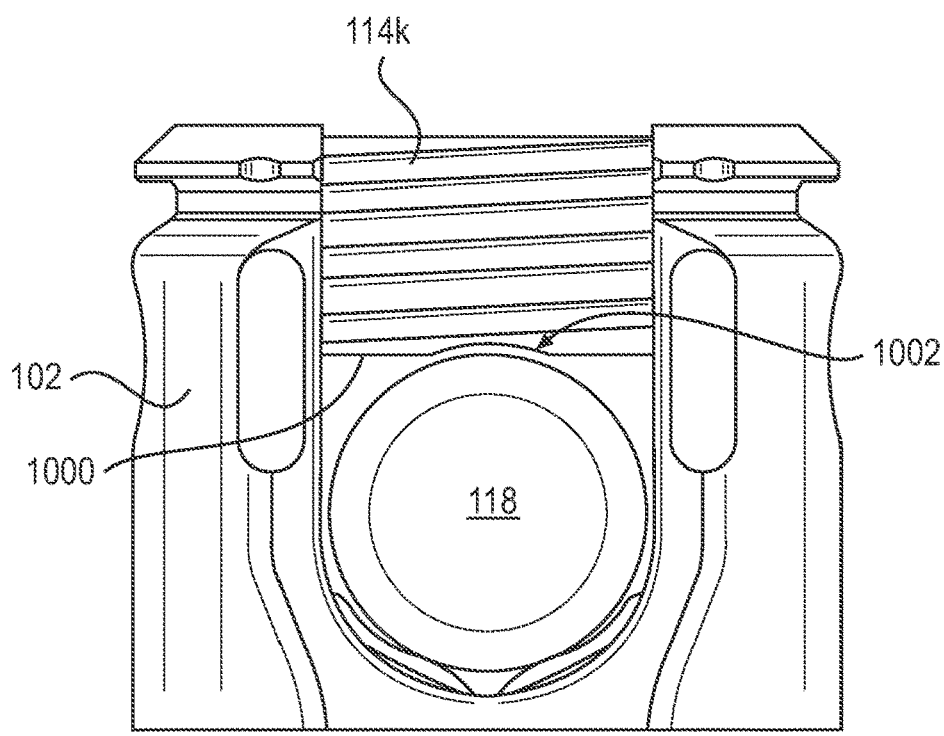
FIG. 10 illustrates a side view of another clamp assembly in accordance with particular embodiments of the present disclosure.

FIG. 10 illustrates a locking cap 114k disposed within the tulip 102 in accordance with particular embodiments of the present disclosure. A bottom 1000 of the locking cap 114k may have a groove 1002 cut into it that seats on the spinal rod 118 as the locking cap 114k rotates to its final tightening state. The groove 1002 may have profile, for example, the matches a profile of the spinal rod 118.

Figure 11:
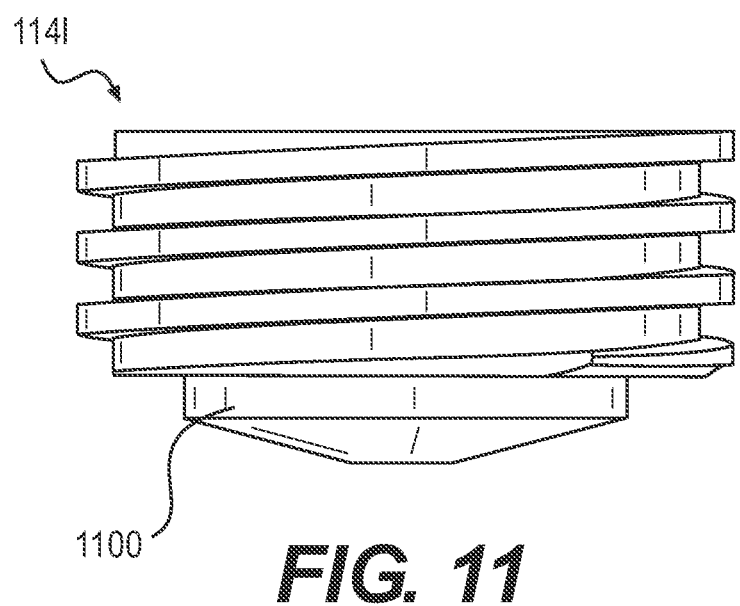
FIG. 11 illustrates a side view of another locking cap in accordance in accordance with particular embodiments of the present disclosure.

FIG. 11 illustrates a locking cap 114L in accordance with particular embodiments of the present disclosure. As shown, a contact surface 1100 for the spinal rod 118 (e.g. shown on FIG. 10) is a separate component to allow the contact surface 1100 to be made from a different material or surface finish from the locking cap 114L. As illustrated, the contact surface 1100 may be attached to a bottom of the locking cap 114L. The contact surface 1100 may be shaped to any of the previously described embodiments. Any suitable technique may used for attachment of the contact surface 1100 to the locking cap 114L, including, but not limited to, adhesives, welding, locking features, and/or fasteners, among others.

Figure 12:
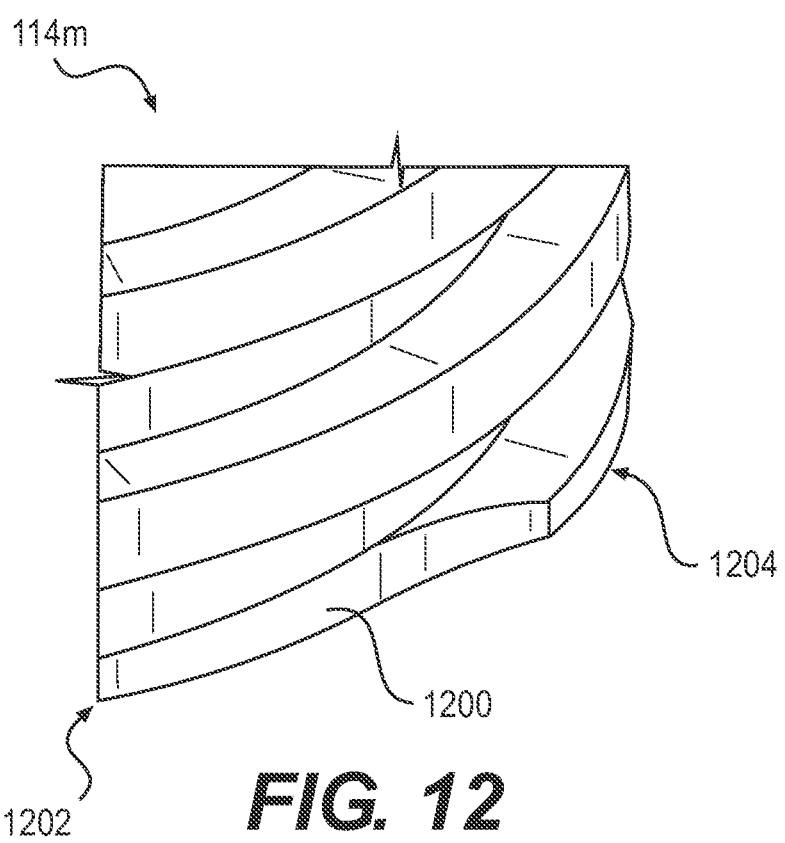
FIG. 12 illustrates a portion of another locking cap in accordance with particular embodiments of the present disclosure.
Figure 13:
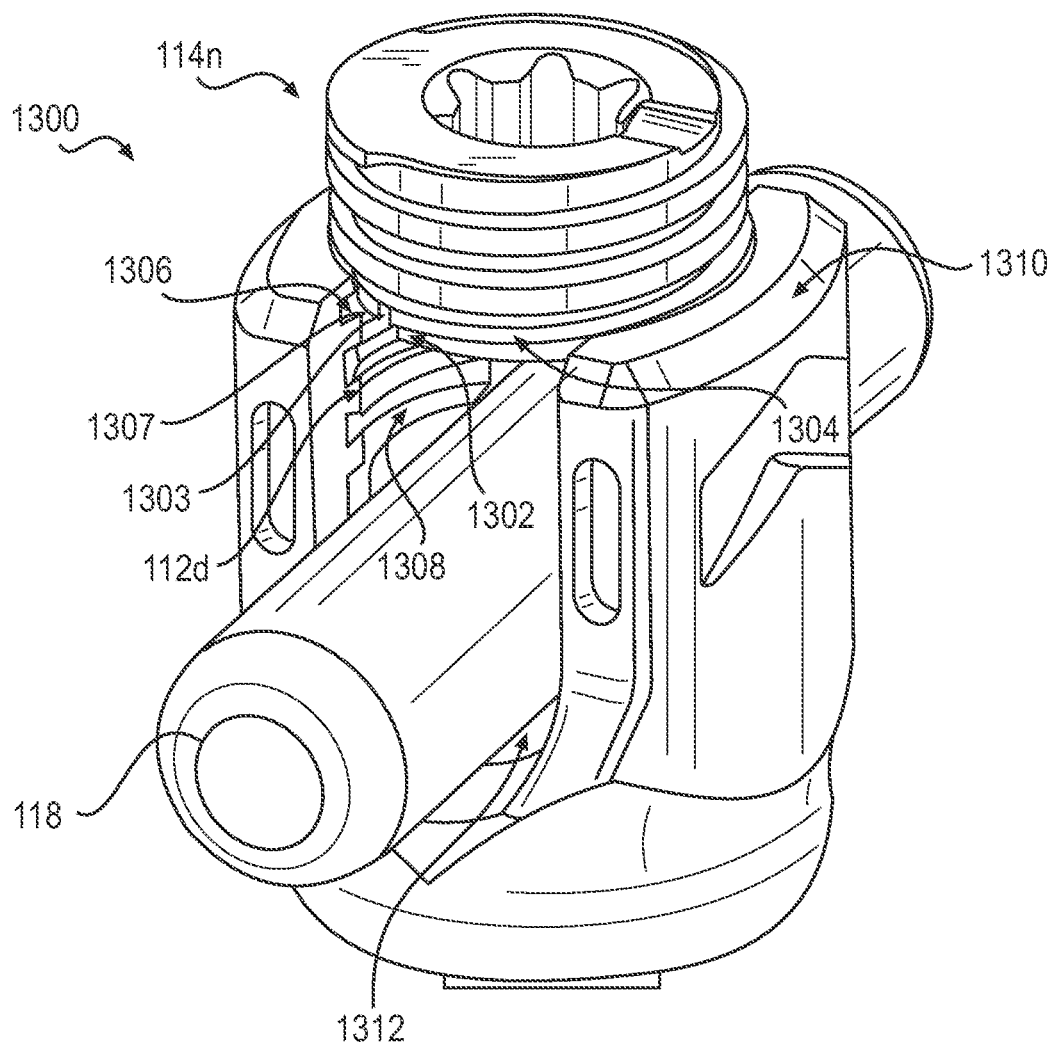
FIG. 13 illustrates a clamp assembly in accordance with particular embodiments of the present disclosure.

Additional features may be included on the locking cap 114. For example, features may be included on the locking cap that increase engagement of the locking cap 114 with the tulip 114 more efficient for installation. FIGS. 12 and 13 illustrate different features that may be included on the locking cap 114 for increasing engagement with the tulip 104.

FIG. 12 illustrates a portion of a locking cap 114m in accordance with particular embodiments of the present disclosure. As shown, a first thread 1204 at a bottom 1202 of the locking cap 114m is broken by a radiused cut 1200 The radiused cut 1120 from the first thread 1200 may increase the strength of the first thread 1200 as it is being engaged and to prevent cross-threading of the locking cap 114m.

FIG. 13 illustrates a clamp assembly 1300 in accordance with particular embodiments of the present disclosure. A start 1302 of threads 1304 in a locking cap 114n and a start 1306 of threads 1308 in an inner surface 112d of a tulip 1310 are timed with corresponding markings such as, for example, cutouts 1303 of the locking cap 114n and marking 1310 of the tulip 1310. When the markings/cutouts 1303 and 1310 are aligned, the start 1302 of the threads 1304 on the locking cap 114n is close to engaging the start 1306 of the threads 1308 on the inner surface 112d of the tulip 1310.

This allows a user to quickly and repeatably engage the threads 1304 of the locking cap 114n with the inner surface 112d of the tulip 1310. The tulip 1310 may have a rounded slot 1312 to accept the spinal rod 118 such that the spinal rod 118 is perpendicular to the threads 1304 of the locking cap 1302.

Figure 14:
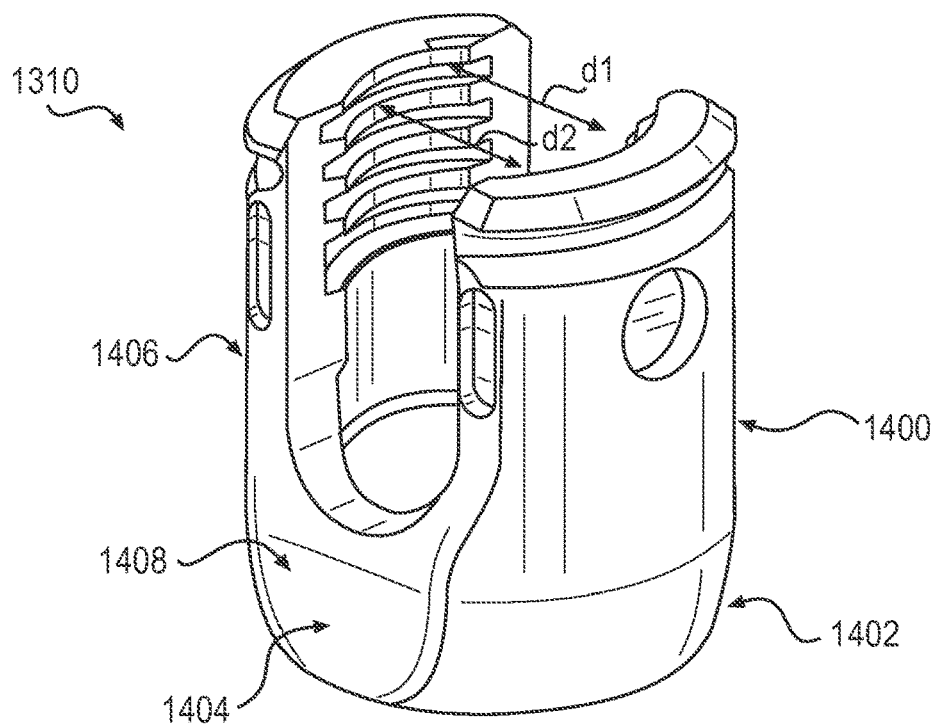
FIG. 14 illustrates a tulip in accordance with particular embodiments of the present disclosure.

FIG. 14 illustrates the tulip 1310 in accordance with particular embodiments of the present disclosure. The sides 1400 of the tulip 1310 may be shaped as a concentric cylinder which taper towards the bottom 1402 of the tulip 1310. A front side 1404 and back side (not shown) are flat, with an upper flat portion 1406 being narrower in width than a lower flat portion 1408.

Figure 15:
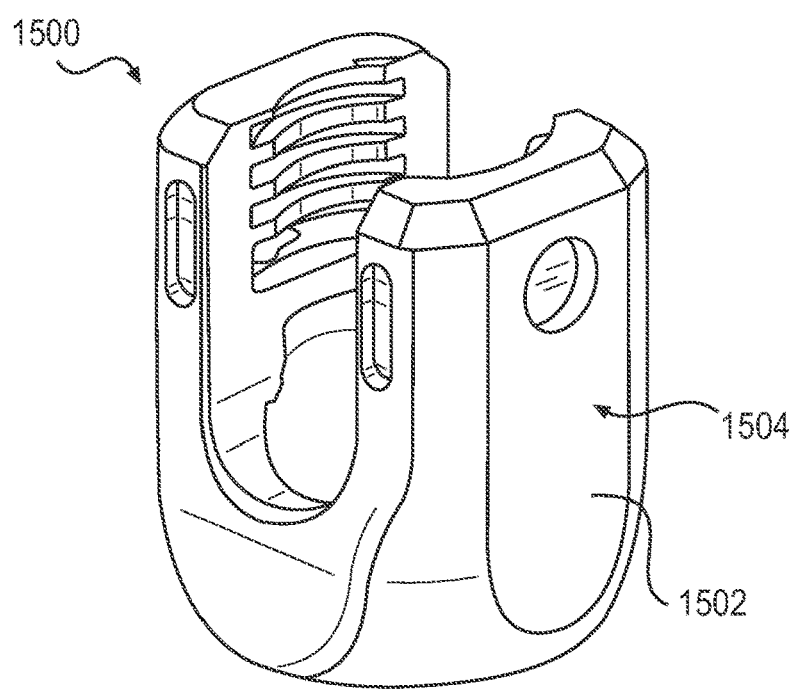
FIG. 15 illustrates another tulip in accordance with particular embodiments of the present disclosure.

FIG. 15 illustrates a tulip 1500 in accordance with particular embodiments of the present disclosure. The tulip 1500 may be similar to the tulip 1310 as shown on FIG. 14. The tulip 1500 may include a large radii or flat portion 1502 on a side 1504 of the tulip 1500. The flat portion 1502 may improve alignment with mating instruments (not shown).

Figures 16A, 16B:
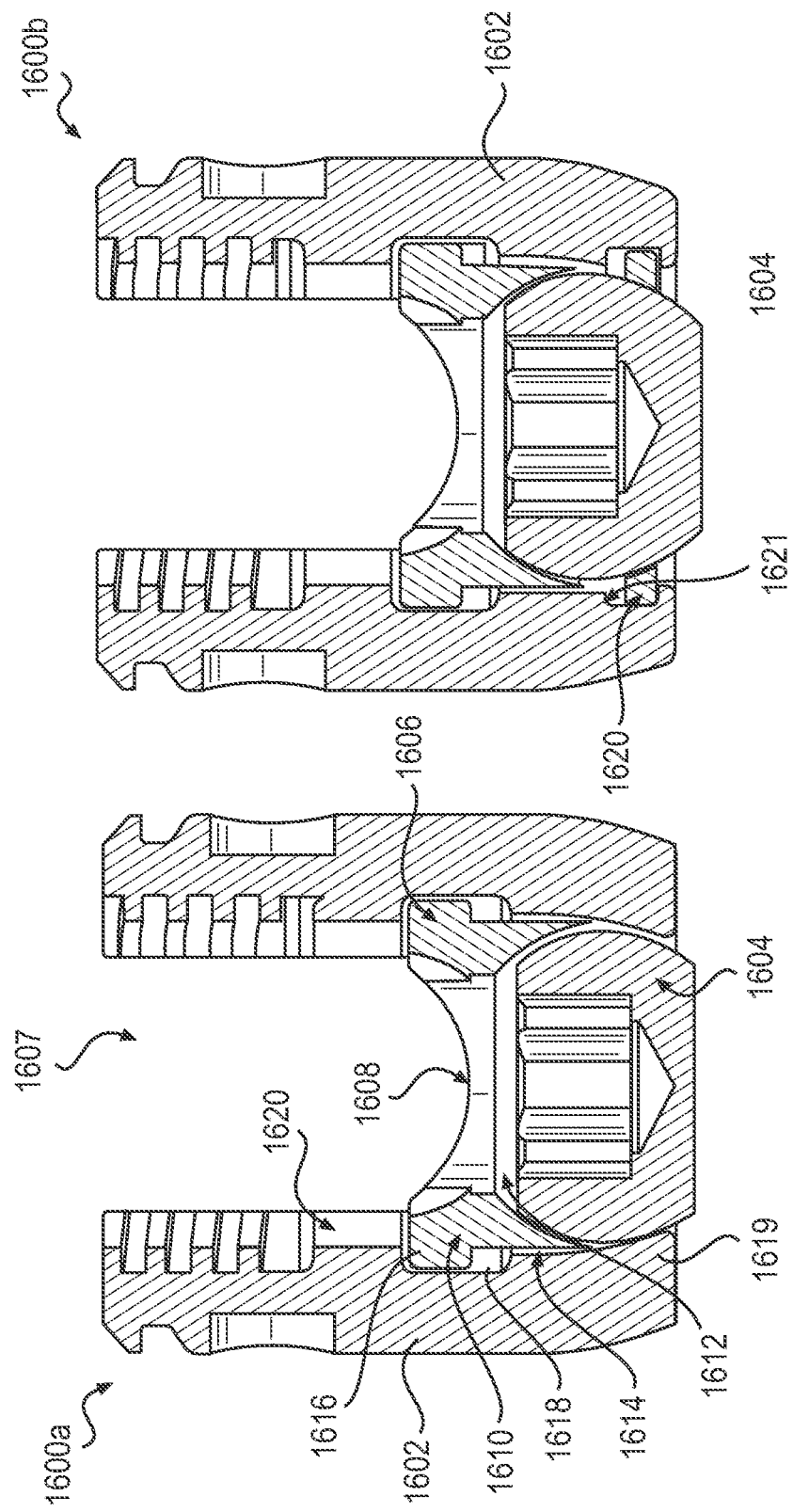
FIG. 16A illustrates a side cross-sectional view of a clamp assembly in accordance with particular embodiments of the present disclosure.
FIG. 16B illustrates a side cross-sectional view of another clamp assembly in accordance with particular embodiments of the present disclosure.

FIG. 16A illustrates a cross-section of a clamp assembly 1600a in accordance with particular embodiments of the present disclosure. The clamp assembly 1600a may include a tulip 1602, a spherical head 1604 of a bone screw, and a saddle 1606.

The saddle 1606 may be movably disposed within an opening 1607, as shown. The saddle 1606 may be an elongated rigid member with a shape similar to the tulip 1602. The saddle 1606 includes an opening 1608 at a first end 1610 and an opening 1612 positioned opposite to the opening 1608 at a second end 1614, as shown. The saddle 1606 may include a ridge 1616 that projects into a recess 1618 extending along an inner surface 1620 of the tulip 1602, thereby preventing movement of the saddle 1606 beyond the recess 1618, as shown. The bone screw 1604 may be disposed within the tulip 1602 and the opening 1612. The opening 1612 may include curvature that corresponds with the shape of the spherical head 1604 to facilitate securing of the spherical head 1604 within the clamp assembly 1600a, as shown. An internal taper 1619 of the tulip 1602 may retain the spherical head 1604. The polyaxial motion is locked when the spinal rod 118 (e.g., shown on FIG. 13) compresses into the saddle 1606 which compresses against the spherical head 1604 of the bone screw.

FIG. 16B illustrates a cross-section of a clamp assembly 1600b and a clip 1620 in accordance with particular embodiments of the present disclosure. The clip 1620 may be used to retain the spherical head 1604 within the tulip 1602 instead of the internal taper 1619 (shown on FIG. 16A) of the tulip 1602. The clip 1620 may be disposed within an internal recess 1621 of the tulip 1602.

Figure 16C:
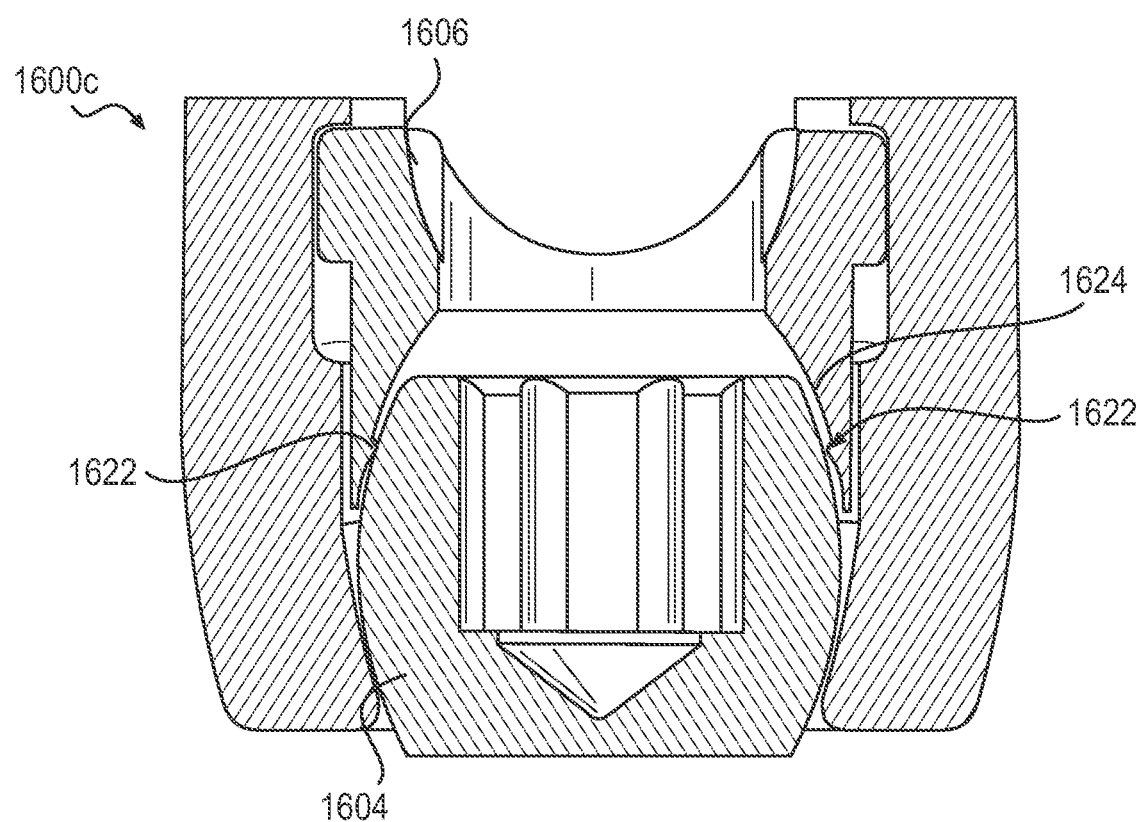
FIG. 16C illustrates a side cross-sectional view of another clamp assembly in accordance with particular embodiments of the present disclosure.

FIG. 16C illustrates a cross-section of a clamp assembly 1600c with circumferential lips 1622 in accordance with particular embodiments of the present disclosure. To create a ring of contact between a saddle 1606a and the spherical head 1604, one or more circumferential lips 1622 on the saddle 1606a or an internal taper 1624 of the saddle 1606a may contact the spherical head 1604.

Figure 17B:
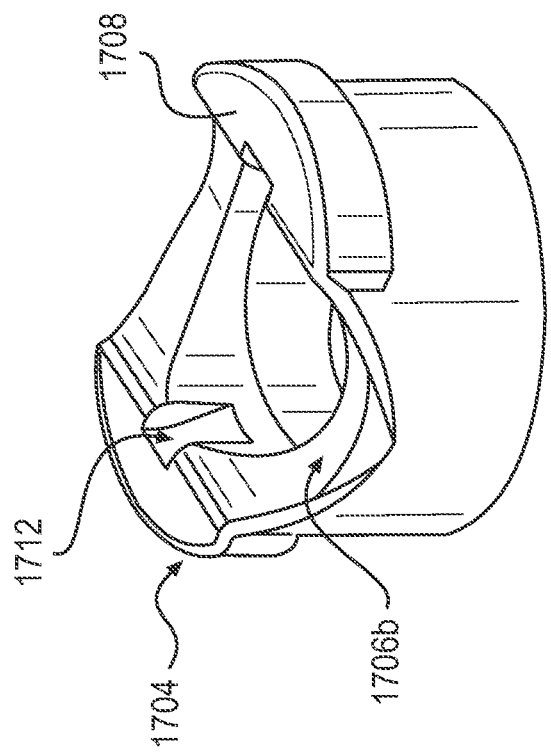
FIG. 17B illustrates a saddle in accordance with particular embodiments of the present disclosure.
Figure 17A:
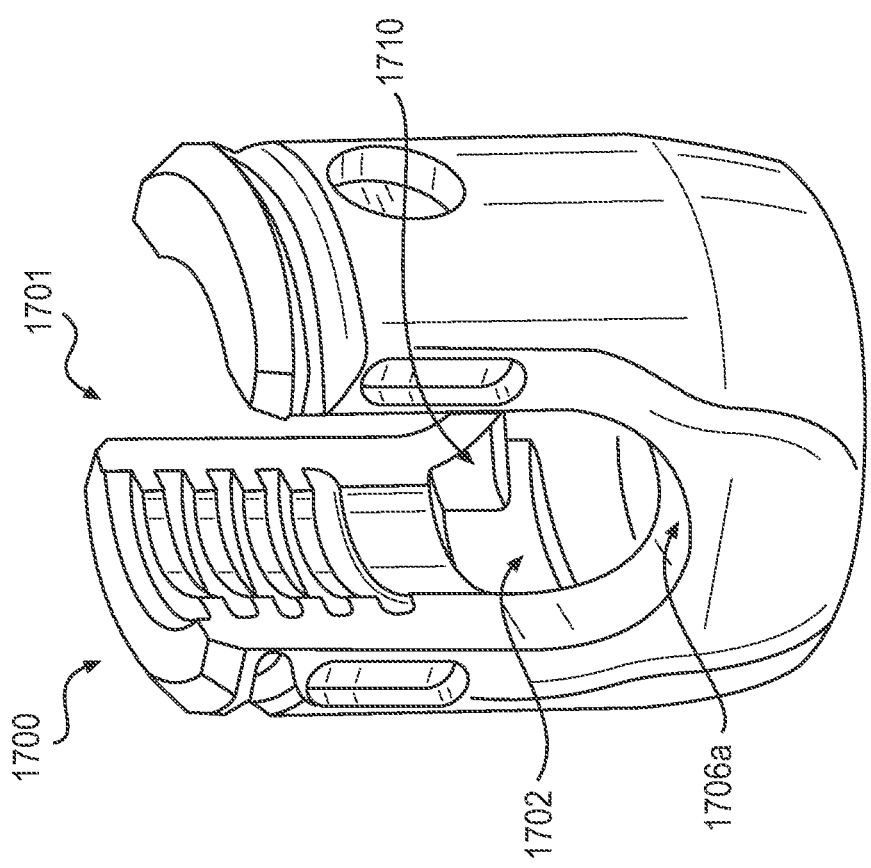
FIG. 17A illustrates a tulip in accordance with particular embodiments of the present disclosure.

FIGS. 17A and 17B illustrate a tulip 1700 and a saddle 1704 in accordance with particular embodiments of the present disclosure. The spherical head 1604 (shown on FIG. 16C) of the bone screw may be inserted into the tulip 1700 and the clip 1620 (shown on FIG. 16B) may be inserted into an internal groove 1702 of the head to retain the spherical head 1604. The saddle 1704 (shown on FIG. 17B) is then inserted from a top 1701 of the tulip 1700 with a spinal rod slot 1706b 90° out of alignment with the rod slot of the tulip 1706a. The saddle is then rotated into the internal groove 1702 so that the rod slots 1706a and 1706b are aligned. An upper profile (e.g., an upper profile 1708 shown on FIG. 17B) of the saddle 1704 and the internal groove 1702 are elliptically shaped to prevent the saddle 1704 from rotating out of alignment. Relief cuts 1710 in the tulip 1700 allow rotation of the saddle 1704 into alignment only in one direction. Grooves 1712 cut into the saddle 1704 allow for an interface with an assembly tool (not shown) to facilitate rotation.

Figure 18:
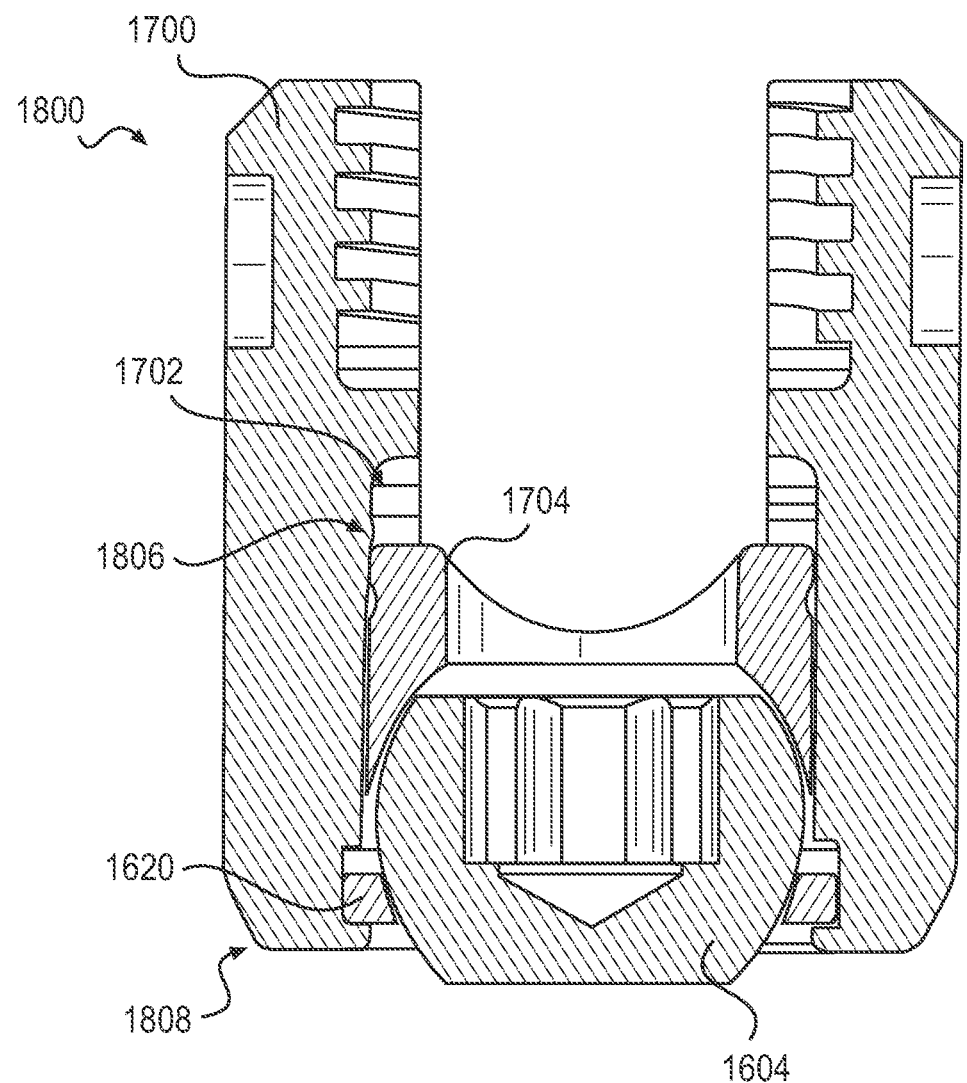
FIG. 18 illustrates a side cross-sectional view of another clamp assembly in accordance with particular embodiments of the present disclosure.

FIG. 18 illustrates a cross-section of a clamp assembly 1800 including the tulip 1700 in accordance with particular embodiments of the present disclosure. In this embodiment, the saddle 1704 may be inserted into the tulip 1700 from the bottom 1808 and pressed past a retaining bump 1806. The spherical head 1604 of the bone screw is then inserted from a bottom 1808 of the tulip 1700 into contact with the saddle 1704 and the clip 1620 inserted from the bottom 1808 to retain the spherical head 1604. The saddle 1704 is then pressed down past the retaining bump 1806. The retaining bump 1806 and elliptical shape of the saddle 1704 and the internal groove 1702 prevent the saddle 1704 from moving upward and rotating.

FIG. 19A illustrates a clamp assembly 1900 in accordance with particular embodiments of the present disclosure. The clamp assembly 1900 may be similar to the clamp assembly 1800. In this embodiment, instead of an ellipse, internal flat portions 1901 of the tulip 1902 are positioned on either side of flat portions 1903 (also shown on FIG. 19B) of a saddle 1904 to restrict rotation of the saddle 1904 within the spinal rod slot 1906.

FIG. 19B illustrates the saddle 1904 in accordance with particular embodiments of the present disclosure. The saddle 1904 includes the flat portions 1903 to correspond with the flat portions 1901 of the tulip 1902 (shown on FIG. 19A).

Figure 20B:
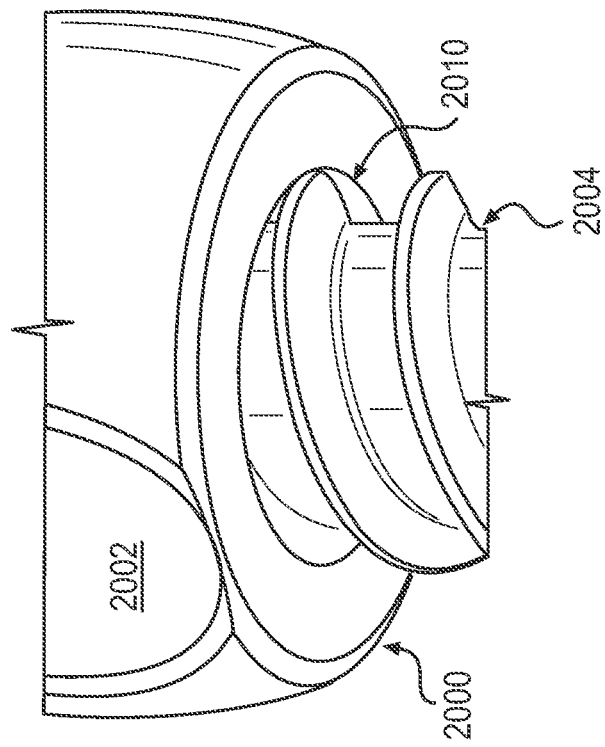
FIG. 20B illustrates a bottom view of a tulip with a bone screw in accordance with particular embodiments of the present disclosure.
Figure 20A:
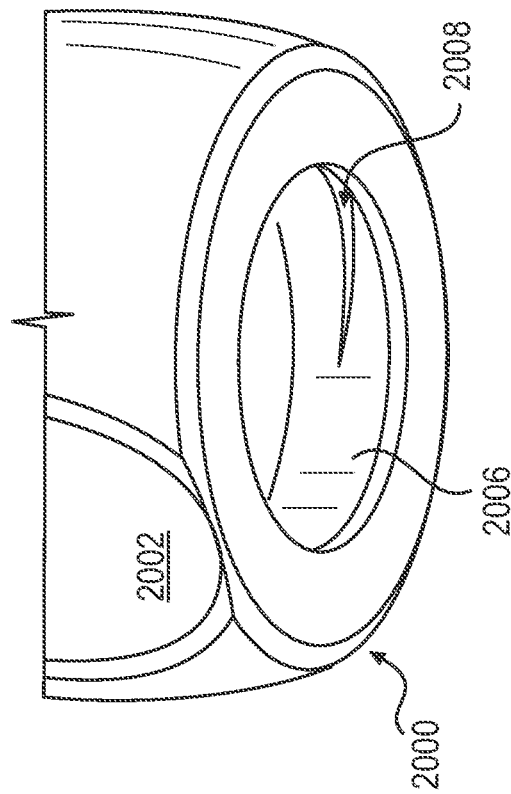
FIG. 20A illustrates a bottom view of a tulip in accordance with particular embodiments of the present disclosure.

FIG. 20A illustrates a bottom 2000 of a tulip 2002 in accordance with particular embodiments of the present disclosure. In this embodiment, a screw 2004 (shown on FIG. 20B) is inserted from a top (e.g., the top 1701 shown on FIG. 17A) of the tulip 2002 until it contacts an internal tapered portion 2006 at the bottom 2000. A saddle (e.g., the saddle 1904 shown on FIG. 19B) may then be inserted from the top of the tulip 2002 and rotated into alignment with a spinal rod slot (e.g., similar to the spinal rod slot 1706a shown on FIG. 17A). Threads 2008 cut into the taper portion 2006 are shaped to allow the largest screw possible to thread through the tulip 2002.

FIG. 20B illustrates the bottom 2000 of the tulip 2002 with the screw 2004 in accordance with particular embodiments of the present disclosure. The screw 2004 extends through a passage 2010 positioned through the bottom 2000 of the tulip 2002.

Figure 21A:
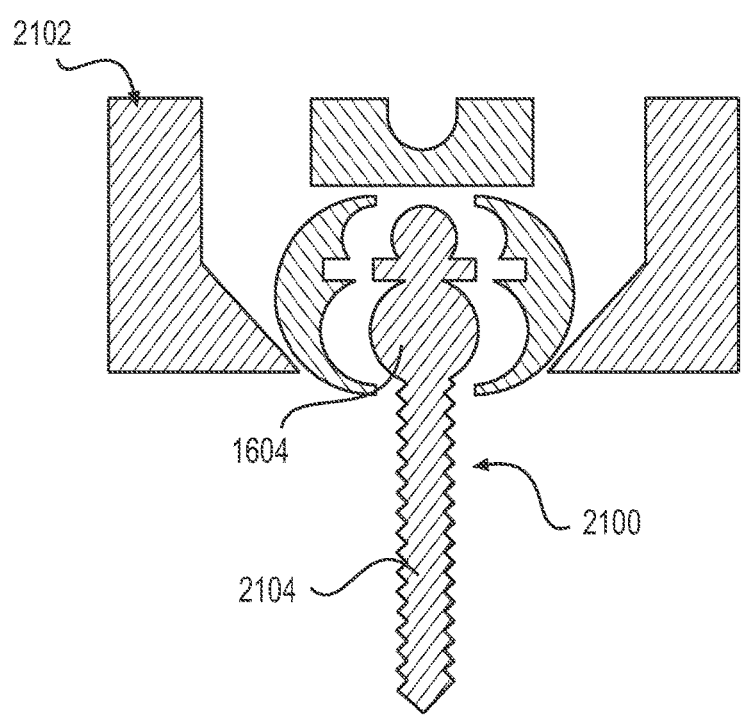
FIG. 21A illustrates a clamp assembly with a bone screw in accordance with particular embodiments of the present disclosure.
Figure 21B:
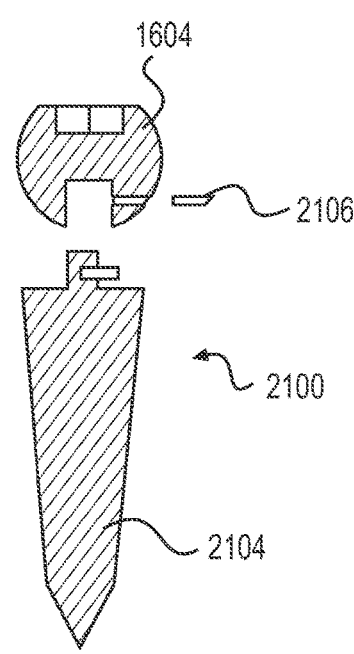
FIG. 21B illustrates a bone screw in accordance with particular embodiments of the present disclosure.

FIGS. 21A and 21B illustrate a bone screw 2100 in accordance with particular embodiments of the present disclosure. The spherical head 1604 of the bone screw 2100 may be inserted into the tulip 2102 before being assembled to the threaded portion 2104 of the bone screw 2100. The threaded portion 2104 of the bone screw 2100 may be retained in the spherical head 1604 by a snap retaining fit, a press fit, a pin, threads, or some combination of retaining features (e.g., retaining feature 2106).

FIG. 21B illustrates the spherical head 1604 separated from the threaded portion 2104 of the bone screw 2100 in accordance with particular embodiments of the present disclosure. The threaded portion 2104 of the bone screw 2100 may be retained in the spherical head 1604 by a snap retaining fit, a press fit, a pin, threads, or some combination of retaining features (e.g., retaining feature 2106).

Figure 22B:
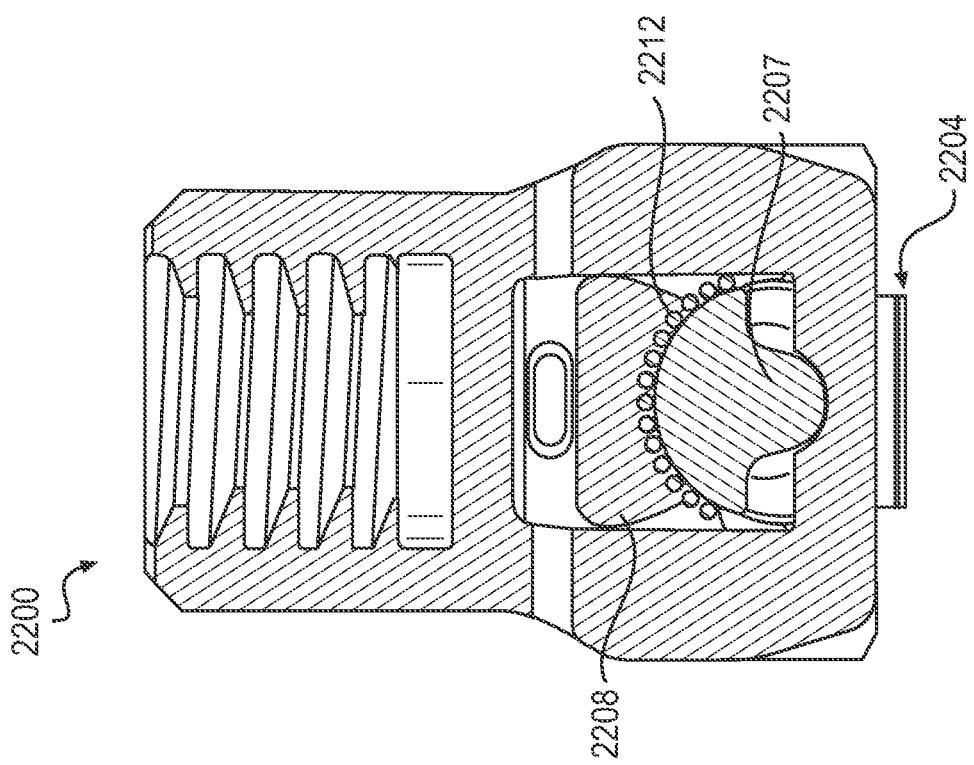
FIG. 22B illustrates a side cross-sectional view of a clamp assembly with a bone screw in accordance with particular embodiments of the present disclosure.
Figure 22A:
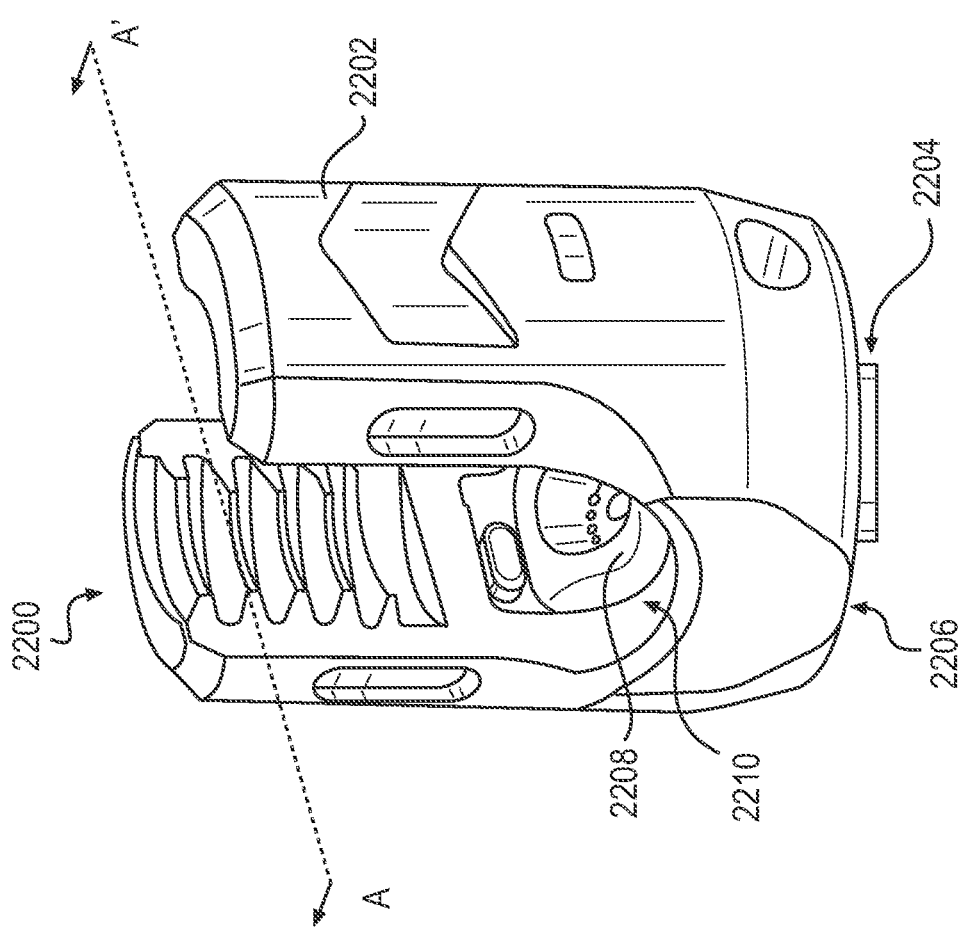
FIG. 22A illustrates a perspective view of a clamp assembly with a pivoting bone screw in accordance with particular embodiments of the present disclosure.

FIG. 22A illustrates a clamp assembly 2200 in accordance with particular embodiments of the present disclosure. The tulip 2202 may be a uniplanar tulip and may include a uniplanar screw 2204. The uniplanar tulip 2202 may have a through hole 2206 which contacts pivots (e.g., pivots 2207 shown on FIG. 22B) on the head of the screw 2204 and allows the head 2208 to pivot either along a spinal rod slot 2210 or perpendicular to the spinal rod slot 2210 depending on the orientation of the through hole 2206. A saddle 2208 compresses against the head 2208 when locked, restricting motion.

FIG. 22B illustrates a cross-section of the clamp assembly 2200, taken along a dashed line extending between A and A', in accordance with particular embodiments of the present disclosure. As previously mentioned, the pivots 2207 allows the head of the screw 2204 to pivot either along the spinal rod slot 2210 (shown on FIG. 22A) or perpendicular to the spinal rod slot 2210. Teeth, groove cuts, or a roughened surface 2212 may increase the grip of this interface.

Figure 23:
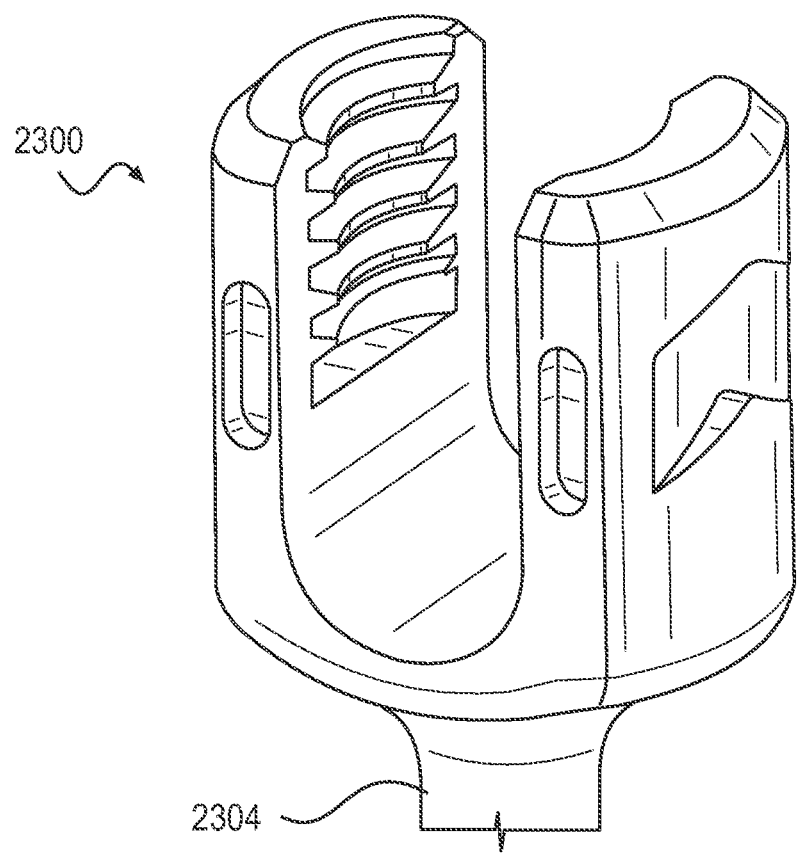
FIG. 23 illustrates a one-piece tulip and bone screw in accordance with particular embodiments of the present disclosure.

FIG. 23 illustrates a monoaxial screw 2300 in accordance with particular embodiments of the present disclosure. The monoaxial screw 2300 combines a screw head (e.g., head 2208 shown on FIG. 22A) with the bone screw portion 2304 into a single component to form the monoaxial screw 2300.

Figure 24A:
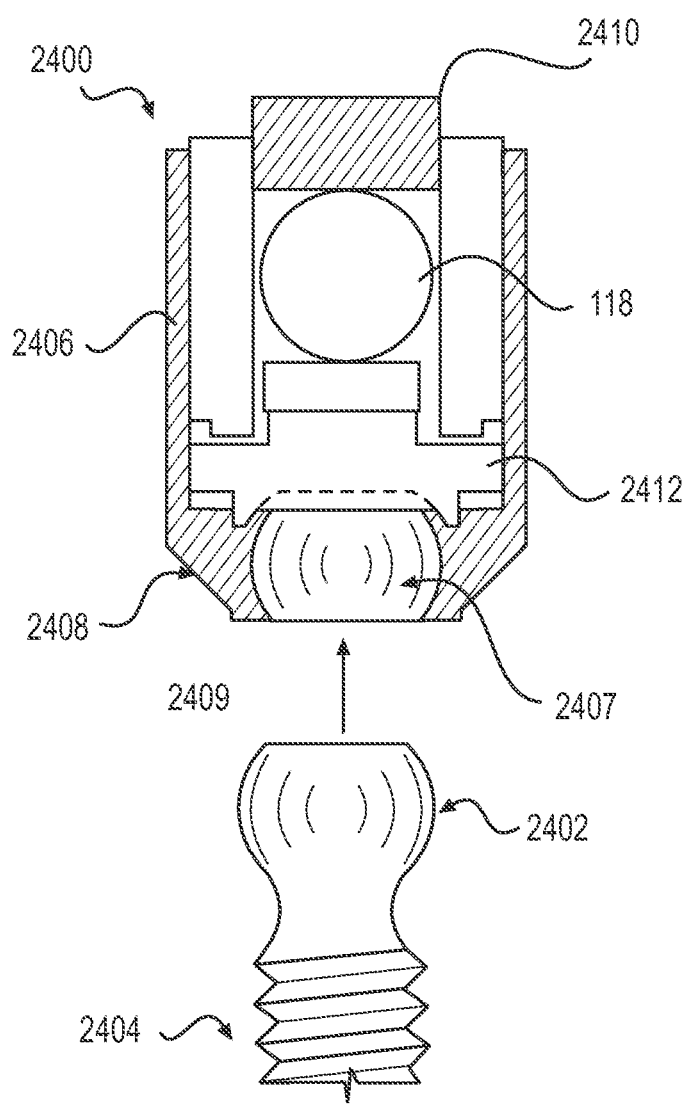
FIG. 24A illustrates a side cross-sectional view of a clamp assembly in accordance with particular embodiments of the present disclosure.

FIG. 24A illustrates a clamp assembly 2400 in accordance with particular embodiments of the present disclosure. The clamp assembly 2400 may include a spherical screw head 2402 of a bone screw 2404 that is splined. The splines on the spherical head 2402 of the bone screw may be cut to follow the spherical profile of the spherical head. The spherical screw head 2402 may be positioned into the tulip 2406 via an opening 2407 at a bottom 2408 of the tulip 2406. The spinal rod 118 may be compressed between a locking cap 2410 and a saddle 2412. The opening 2407 may include conical splines 2409 to mate with splines (e.g., splines 2403 shown on FIG. 24B) of the spherical screw head 2402.

Figure 24B:
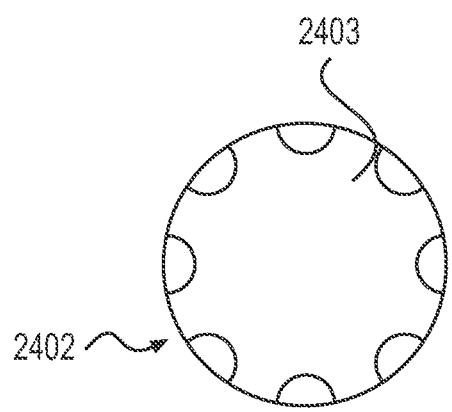
FIG. 24B illustrates a top view of a head of a bone screw in accordance with particular embodiments of the present disclosure.

FIG. 24B illustrates a top view of the spherical screw head 2402 in accordance with particular embodiments of the present disclosure. The splines 2403 on the spherical screw head 2402 includes a circular profile and may mate with similarly shaped splines 2409 cut into the opening 2407 (shown on FIG. 24A). These splines 2403 do not allow the tulip 2402 to rotate about the bone screw 2404, but permit medial and lateral angulation. Axial torque can be transmitted to the bone screw 2404, allowing the bone screw 2404 to be driven or reversed without engaging a drive feature, (e.g., drive feature shown on FIGS. 4A and 4B) or by an instrument (not shown) not positioned coaxially with the bone screw.

Various instrument interfaces may be used for engaging insertion, positioning, reduction, and derotation instruments. The bone screw (e.g., the bone screw 2404) may include a hex, hexalobe, or modified hexalobe in the spherical screw head for driving the bone screw into a bone. Features on the tulips in the embodiments below may be engaged by instruments with corresponding tabs or grooves which collapse, pivot, slide, or flex into engagement with the tulip for insertion, positioning, reduction, and derotation.

FIG. 25A illustrates an inner surface 2500a of a tulip (e.g., similar to the tulip 102 shown on FIG. 1) in accordance with particular embodiments of the present disclosure. In this embodiment cylindrical, elliptical, or linear grooves 2502a may be cut into the inner surface 2500a to receive a instrument (not shown).

FIG. 25B illustrates an inner surface 2500b of a tulip (e.g., similar to the tulip 102 shown on FIG. 1) in accordance with particular embodiments of the present disclosure. In this embodiment cylindrical, elliptical, or linear grooves 2502b may be cut into the inner surface 2500b to receive a driving instrument (not shown). As shown, the linear grooves 2502b are smaller (e.g., shorter and/or shallower) in size than the linear grooves 2502a of FIG. 25A.

FIG. 26A illustrates a tulip 2600 in accordance with particular embodiments of the present disclosure. The tulip 2600 may include an upper outer section 2602a that includes a ledge, lip, or groove 2604a, as shown.

FIG. 26B illustrates a portion 2606a of a tulip (e.g., similar to the tulip 2600 shown on FIG. 26A) in accordance with particular embodiments of the present disclosure. The portion 2606a may include an upper outer section 2602b that includes a lip 2604b and a groove 2608a that includes an upper surface 2609a that is angled inward, as shown. A bottom surface 2610a is horizontal. The inward angle prevents disengagement of an instrument (not shown) under axial reduction loads.

FIG. 26C illustrates a portion 2606b of a tulip (e.g., similar to the tulip 2600 shown on FIG. 26A) in accordance with particular embodiments of the present disclosure. The portion 2606b may include an upper outer section 2602c that includes the lip 2604b and a groove 2608b that includes the upper surface 2609a that is angled inward, as shown. A bottom surface 2610b is angled outward. The inward angle prevents disengagement of an instrument (not shown) under axial reduction loads.

FIG. 26D illustrates a portion 2606c of a tulip (e.g., similar to the tulip 2600 shown on FIG. 26A) in accordance with particular embodiments of the present disclosure. The portion 2606c may include an upper outer section 2602d that includes a lip 2604c and a groove 2608c that includes an upper surface 2609b that is flanged, as shown. The bottom surface 2610a is flat. The flange prevents disengagement of an instrument (not shown) under axial reduction loads.

FIG. 26E illustrates a portion 2606d of a tulip (e.g., similar to the tulip 2600 shown on FIG. 26A) in accordance with particular embodiments of the present disclosure. The portion 2606d may include an upper outer section 2602e that includes a lip 2604d and a groove 2608d that includes the upper surface 2609b that is flanged, as shown. The bottom surface 2610a is angled outward. The flange prevents disengagement of an instrument (not shown) under axial reduction loads.

FIG. 26F illustrates a portion 2606e of a tulip (e.g., similar to the tulip 2600 shown on FIG. 26A) in accordance with particular embodiments of the present disclosure. The portion 2606e may include an upper outer section 2602f that includes the lip 2604e and a groove 2608e that includes the upper surface 2609a that is angled inward, as shown. A bottom surface 2610e is angled inward. The inward angles prevent disengagement of an instrument (not shown) under axial reduction loads.

FIG. 26G illustrates a portion 2606f of a tulip (e.g., similar to the tulip 2600 shown on FIG. 26A) in accordance with particular embodiments of the present disclosure. The portion 2606f may include an upper outer section 2602g that includes the lip 2604a without a bottom surface.

FIG. 26H illustrates a portion 2606g of a tulip (e.g., similar to the tulip 2600 shown on FIG. 26A) in accordance with particular embodiments of the present disclosure. The portion 2606g may include an upper outer section 2602h that includes a lip 2604g and a groove 2608f that includes the upper surface 2609b that is flanged, as shown. A bottom surface 2610f is also flanged. The flanges prevent disengagement of an instrument (not shown) under axial reduction loads.

FIG. 26i illustrates a portion 2606h of a tulip (e.g., similar to the tulip 2600 shown on FIG. 26A) in accordance with particular embodiments of the present disclosure. The portion 2606h may include an upper outer section 2602i that includes a lip 2604h and a groove 2608g. A cross-section of the groove 2608g is circular with a depth greater than the radius of the groove to prevent disengagement of an instrument (not shown) under axial reduction loads.

FIG. 26j illustrates a portion 2606i of a tulip (e.g., similar to the tulip 2600 shown on FIG. 26A) in accordance with particular embodiments of the present disclosure. The portion 2606i may include an upper outer section 2602j that includes a lip 2604i and a groove 2608h, as shown. A second groove 2612 may be disposed on a top of the portion 2606i, as shown, to allow insertion of a tip of an instrument (not shown) to resist outward splaying forces under axial reduction loads.

FIG. 26K illustrates a section view of an upper portion of FIGS. 26B-J in accordance with particular embodiments of the present disclosure. As shown, upper portion 2614 which may include the upper portion 2604c and/or 2604d may be cylindrical.

Figure 27:
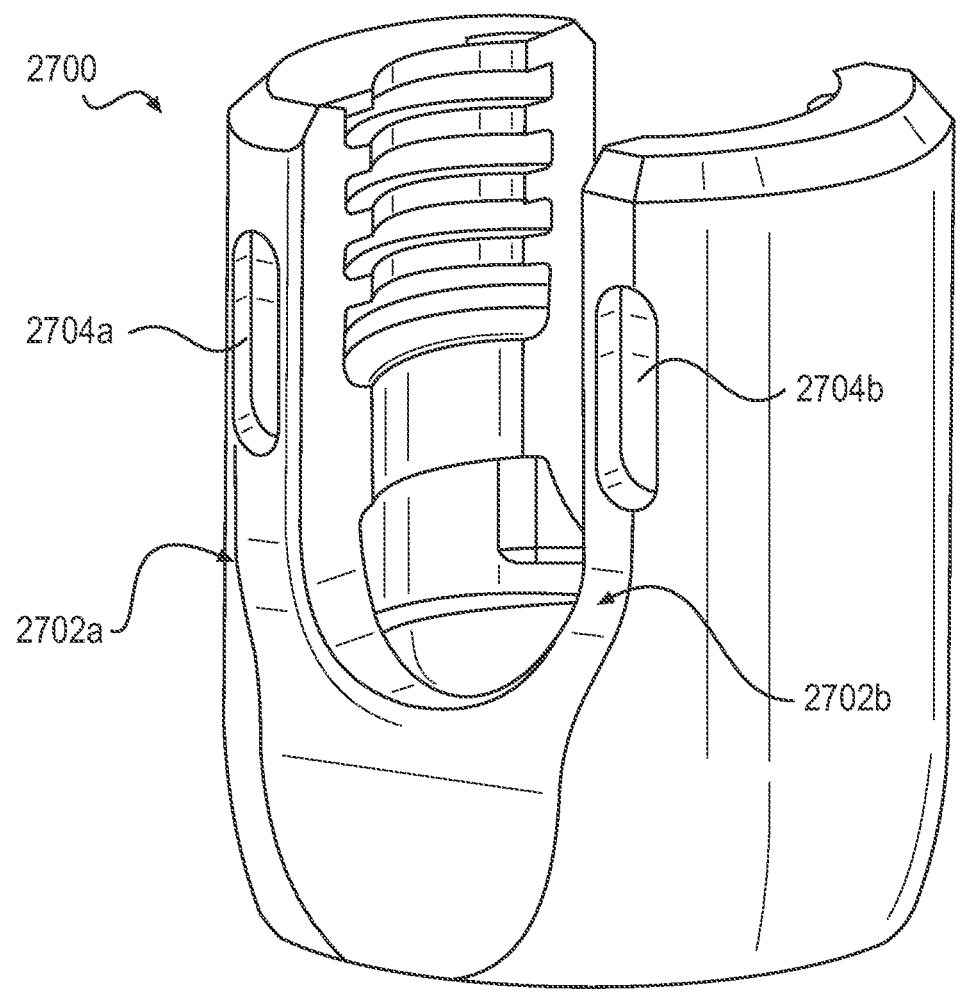

FIG. 27 illustrates a tulip 2700 in accordance with embodiments of the present disclosure. The tulip 2700 may be similar to the tulip 102 (shown on FIG. 1). The tulip 2700 may include front portions 2702a and 2702b that include vertical slots 2704a and 2704b which are engaged by corresponding tabs on an instrument. A rear portion (not shown) may be similar to the front side (shown).

FIG. 28 illustrates a tulip 2800 in accordance with embodiments of the present disclosure. The tulip 2800 may be similar to the tulip 102 (shown on FIG. 1). The tulip 2800 may include side portions 2802a and 2802b. The side portion 2802a includes a circular pocket 2804a which is engaged by corresponding tabs on an instrument. The side portion 2802b may be similar to the side portion 2802a.

FIG. 29 illustrates a tulip 2900 in accordance with embodiments of the present disclosure. The tulip 2900 may be similar to the tulip 102 (shown on FIG. 1). The tulip 2900 may include side portions 2902a and 2902b. The side portion 2902a includes a chevron which is engaged by corresponding tabs on an instrument. The side portion 2902b may be similar to the side portion 2902a.

Figure 30:
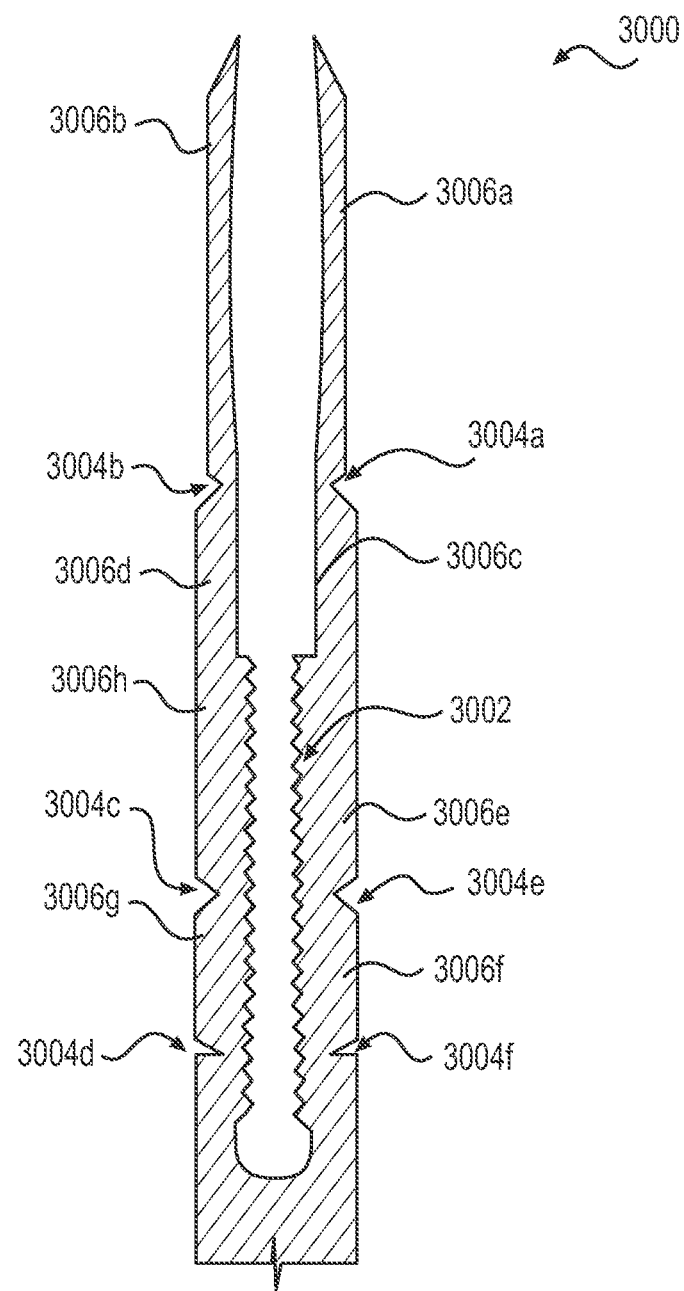
FIG. 30 illustrates a clamp assembly with break off portions in accordance with particular embodiments of the present disclosure.

FIG. 30 illustrates a tulip 3000 in accordance with embodiments of the present disclosure. The tulip 3000 may be similar to the tulip 102 (shown on FIG. 1). The tulip 3000 may include a threaded upper portion 3002 that may be extended to allow a spinal rod (e.g., the spinal rod 118 shown on FIG. 13) to be captured and reduced into the tulip 3000 by threading a locking cap (e.g., the threaded locking cap 114 shown on FIG. 1). Internal and/or external grooves 3004a-3004f allow for extended tabs 3006a-3006h to be broken away from the tulip 3000 once they are no longer needed. The multiple grooves 3004a-3004f at different heights allow tabs 3006a-3006h to be broken at a desired height to reduce the amount of turns necessary to turn the locking cap, or prevent contact with adjacent implants.

Figure 31B:
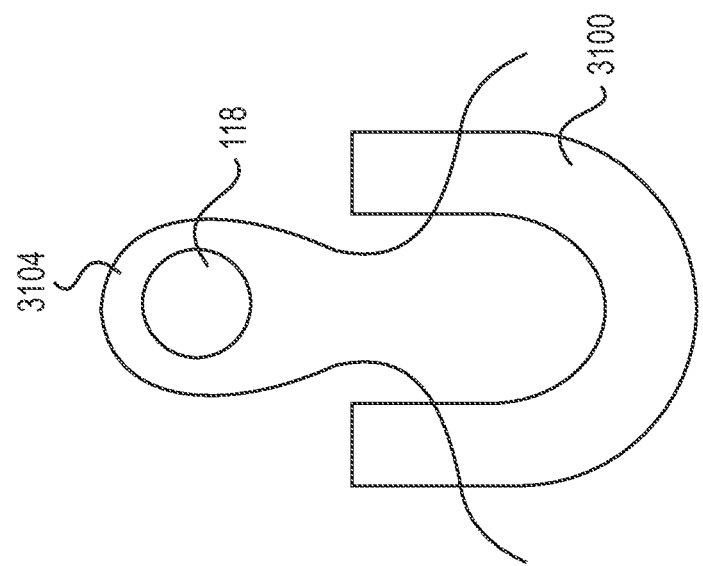
FIG. 31B illustrates a tulip with a cable positioned about a spinal rod in accordance with particular embodiments of the present disclosure.
Figure 31A:
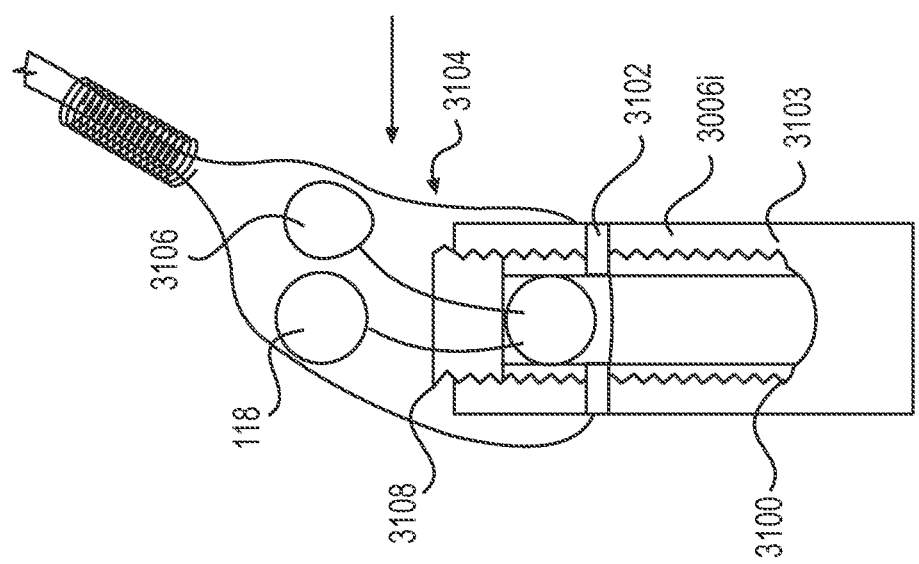
FIG. 31A illustrates a clamp assembly with a cable in accordance with particular embodiments of the present disclosure.

FIG. 31A illustrates a tulip 3100 in accordance with embodiments of the present disclosure. The tulip 3100 may be similar to the tulip 3000 (shown on FIG. 30). In this embodiment, a hole 3102 through a side of a tab 3006i allows for passage of a cable 3104. When looped around the spinal rod 118 or a mating instrument 3106, tensioning of the cable 3104 reduces the spinal rod 118 into the tulip 3100 before being captured by a locking cap 3108. In certain embodiments, the holes 3102 may be in sides 3103 of the tulip 3100 without the tab 3006i.

FIG. 31B illustrates a close-up of the tulip 3100 in accordance with embodiments of the present disclosure. As shown, the cable 3104 is positioned about the spinal rod 118 and extends through the tulip 3100.

The present disclosure as described above describes many features which allow improved functionality, strength, and ease of manufacturing for a pedicle screw head. The locking cap designs describe thread geometries that improve strength, reduce outward splaying forces on the screw head, increase resistance to cross-threading, allows quick engagement of the locking cap, a more consistent interface with mating instruments, and contacts with the spinal rod to increase gripping strength. The internal component designs describe multiple features to allow simplified geometries to reduce profile, increase polyaxial strength, and simplify manufacturing and assembly. The uniplanar, monoaxial, and axially constrained polyaxial screw designs allow for rigidity in various directions to allow the user to transmit forces to the vertebral body for correction or screw insertion. The instrument interfaces describe a variety of features to allow instruments to interface from several directions, provide increased holding strength, decrease splaying forces which would cause disengagement of instruments, and simplify manufacturing. The reduction tab designs allow for a new method for reducing the rod into the screw head.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. A clamp assembly comprising:
   a tulip comprising an opening comprising an inner surface, wherein the inner surface is threaded;
   a threaded locking cap disposed in the opening;
   a saddle configured to be positioned within the tulip, the saddle having flat portions corresponding with flat portions on the tulip, to restrict rotation of the saddle, wherein the diameter of an upper portion of the saddle including the flat portions is smaller than the diameter of a lower portion of the saddle; and
   a clip positioned within a groove on a bottom portion of the tulip, wherein the clip retains a head of screw within the clamp assembly,
   a driving instrument having a distal end with spring tabs;
   wherein the threaded locking cap includes grooves for receiving the spring tabs of a driving instrument,
   wherein the spring tabs are configured to clip into the grooves of the locking cap to secure the driving instrument to the locking cap.

2. The clamp assembly of claim 1, wherein top surfaces of threads of the inner surface are rectangular and wherein bottom surfaces of threads of the inner surface are angled.

3. The clamp assembly of claim 2, wherein top surfaces of threads of the threaded locking cap are rectangular and wherein bottom surfaces of threads of the locking cap are angled.

4. A clamp assembly comprising:
   a tulip comprising an opening comprising an inner surface, wherein the inner surface is threaded; and
   a threaded locking cap disposed in the opening, wherein the threaded locking cap includes a drive feature,
   a saddle configured to be positioned within the tulip, the saddle having flat portions corresponding with flat portions on the tulip, to restrict rotation of the saddle wherein the diameter of an upper portion of the saddle including the flat portions is smaller than the diameter of a lower portion of the saddle; and a clip positioned within a groove on a bottom portion of the tulip, wherein the clip retains a head of screw within the clamp assembly, a driving instrument having a distal end with spring tabs;

wherein the drive feature of the threaded locking cap includes grooves for receiving spring tabs of a driving instrument, wherein the spring tabs are configured to clip into the grooves of the locking cap to secure the driving instrument to the locking cap.

5. The clamp assembly of claim 4, wherein a bottom of the threaded locking cap comprises a tapered flat portion.

6. The clamp assembly of claim 4, wherein a bottom of the threaded locking cap comprises a rounded bump.

7. The clamp assembly of claim 4, wherein a bottom of the threaded locking cap comprises a rounded ring configured to contact a spinal rod at two points.

8. The clamp assembly of claim 4, wherein a bottom of the threaded locking cap comprises a groove configured to seat on a spinal rod.

9. The clamp assembly of claim 4, wherein a bottom of the threaded locking cap comprises a contact component made of a different material than the threaded locking cap.

10. The clamp assembly of claim 4, wherein an outer surface of the tulip comprises grooves configured to receive a driving instrument.

11. A clamp assembly comprising:

a tulip, wherein an inner surface of the tulip comprises threads; and a drive feature positioned in an outer portion of the tulip, the drive feature configured to receive a driving instrument a threaded locking cap disposed in the opening;

a saddle configured to be positioned within the tulip, the saddle having flat portions corresponding with flat portions on the tulip, to restrict rotation of the saddle wherein the diameter of an upper portion of the saddle including the flat portions is smaller than the diameter of a lower portion of the saddle; and a clip positioned within a groove on a bottom portion of the tulip, wherein the clip retains a head of screw within the clamp assembly, a driving instrument having a distal end with spring tabs;

wherein the threaded locking cap includes grooves for receiving spring tabs of a driving instrument, wherein the spring tabs are configured to clip into the grooves of the locking cap to secure the driving instrument to the locking cap.

12. The clamp assembly of claim 11, wherein the feature comprises a pocket in a shape of a chevron, a vertical slot, or a circle.

* * * * *